United States Patent
Xu et al.

(10) Patent No.: US 12,194,033 B2
(45) Date of Patent: Jan. 14, 2025

(54) GLYCINE RECEPTOR MODULATORS AND METHODS OF USE

(71) Applicant: University of Pittsburgh—Of the Commonwealth System of Higher Education, Pittsburgh, PA (US)

(72) Inventors: Yan Xu, Pittsburgh, PA (US); Pei Tang, Pittsburgh, PA (US); Marta Megan Wells, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 161 days.

(21) Appl. No.: 17/940,803

(22) Filed: Sep. 8, 2022

(65) Prior Publication Data

US 2023/0097618 A1 Mar. 30, 2023

Related U.S. Application Data

(62) Division of application No. 16/631,422, filed as application No. PCT/US2018/042162 on Jul. 13, 2018, now Pat. No. 11,484,532.

(60) Provisional application No. 62/598,951, filed on Dec. 14, 2017, provisional application No. 62/534,127, filed on Jul. 18, 2017.

(51) Int. Cl.
| | |
|---|---|
| *A61K 31/452* | (2006.01) |
| *A61K 31/166* | (2006.01) |
| *A61K 31/485* | (2006.01) |
| *A61K 31/495* | (2006.01) |
| *A61P 25/04* | (2006.01) |
| *A61P 25/36* | (2006.01) |
| *A61K 45/06* | (2006.01) |

(52) U.S. Cl.
CPC .......... *A61K 31/452* (2013.01); *A61K 31/166* (2013.01); *A61K 31/485* (2013.01); *A61K 31/495* (2013.01); *A61P 25/04* (2018.01); *A61P 25/36* (2018.01); *A61K 45/06* (2013.01)

(58) Field of Classification Search
CPC .................................................. A61K 31/452
See application file for complete search history.

(56) References Cited

U.S. PATENT DOCUMENTS

| | | | |
|---|---|---|---|
| 4,906,655 A | 3/1990 | Horwell et al. | |
| 5,514,680 A | 5/1996 | Weber et al. | |
| 11,484,532 B2 * | 11/2022 | Xu | A61P 25/36 |

FOREIGN PATENT DOCUMENTS

WO WO 94/00124 1/1994

OTHER PUBLICATIONS

Benyamin et al., "Opioid complications and side effects," *Pain Physician*, 11(2 Suppl.): S105-20, Mar. 2008.
CAS Registry No. 1061455-79-5 entered Oct. 14, 2008.
CAS Registry No. 1209692-97-6 entered Mar. 14, 2010.
CAS Registry No. 1355735-62-4 entered Feb. 7, 2012.
Halfpenny et al., "Highly Selective κOpioid Analgesics. Synthesis of Some Conformationally Restricted Naphthalene Derivatives with High Receptor Affinity and Selectivity," *Journal of Medicinal Chemistry*, 34(1): 190-194, Jan. 31, 1991.
Harvey et al., "GlyR α3: an essential target for spinal $PGE_2$-mediated inflammatory pain sensitization," *Science*, 304(5672): 884-887, May 7, 2004.
Hejazi et al., "$\Delta^9$-tetrahydrocannabinol and endogenous cannabinoid anandamide directly potentiate the function of glycine receptors," *Molecular Pharmacology*, 69(3): 991-997, Mar. 2006.
International Search Report and Written Opinion issued for International Application No. PCT/US2018/042162 on Aug. 14, 2018.
Mowrey et al., "Open-channel structures of the human glycine receptor α1 full-length transmembrane domain," *Structure*, vol. 21, pp. 1987-1904, Oct. 8, 2013.
Pacher et al., "The endocannabinoid system as an emerging target of pharmacotherapy," *Pharmacological Reviews*, 58(3): 389-462, Sep. 2006.
Wells et al., "Ensemble-based virtual screening for cannabinoid-like potentiators of the human glycine receptor α1 for the treatment of pain," *J. Med. Chem.*, 58(7):2958-2966, Apr. 9, 2015.
Xiong et al., "Cannabinoid potentiation of glycine receptors contributes to cannabis-induced analgesia," *Nat. Chem. Biol.*, 7(5): 296-303, May 2011.
Xiong et al., "Cannabinoids suppress inflammatory and neuropathic pain by targeting α3 glycine receptors," *J. Exp. Med.*, 209(6): 1121-1134, May 14, 2012.

\* cited by examiner

*Primary Examiner* — Svetlana M Ivanova
(74) *Attorney, Agent, or Firm* — Klarquist Sparkman, LLP

(57) ABSTRACT

Compounds and methods for modulating the activity of receptors are disclosed. Some of the compounds modulate the activity of glycine receptors. Certain embodiments of the compounds are useful for treatment of pain, treatment of opioid addiction, and/or reduction of side effects attributable to opioid use.

17 Claims, 15 Drawing Sheets compound 1 compound 2 compound 3 compound 4 compound 5 compound 6 compound 7 compound 8

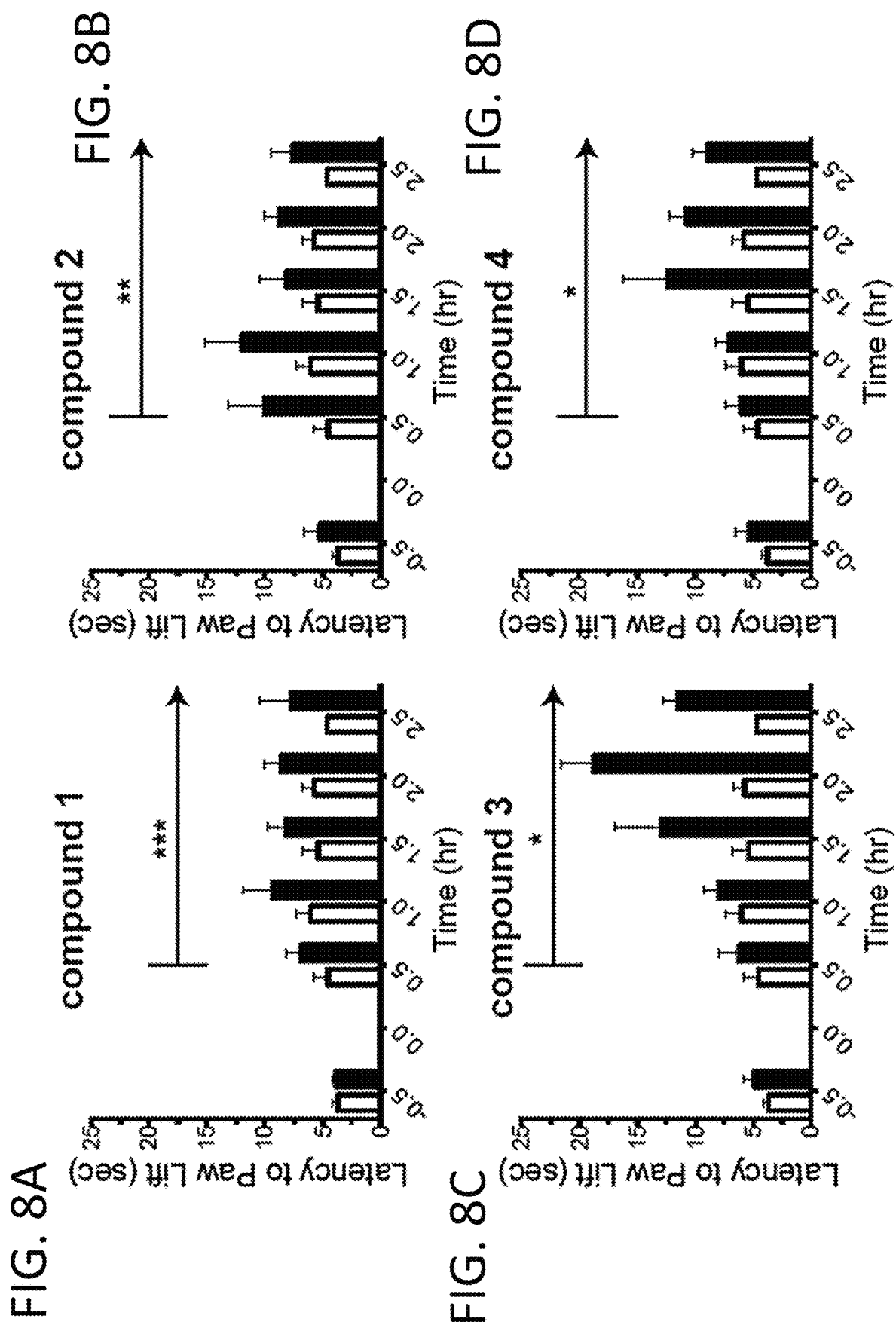

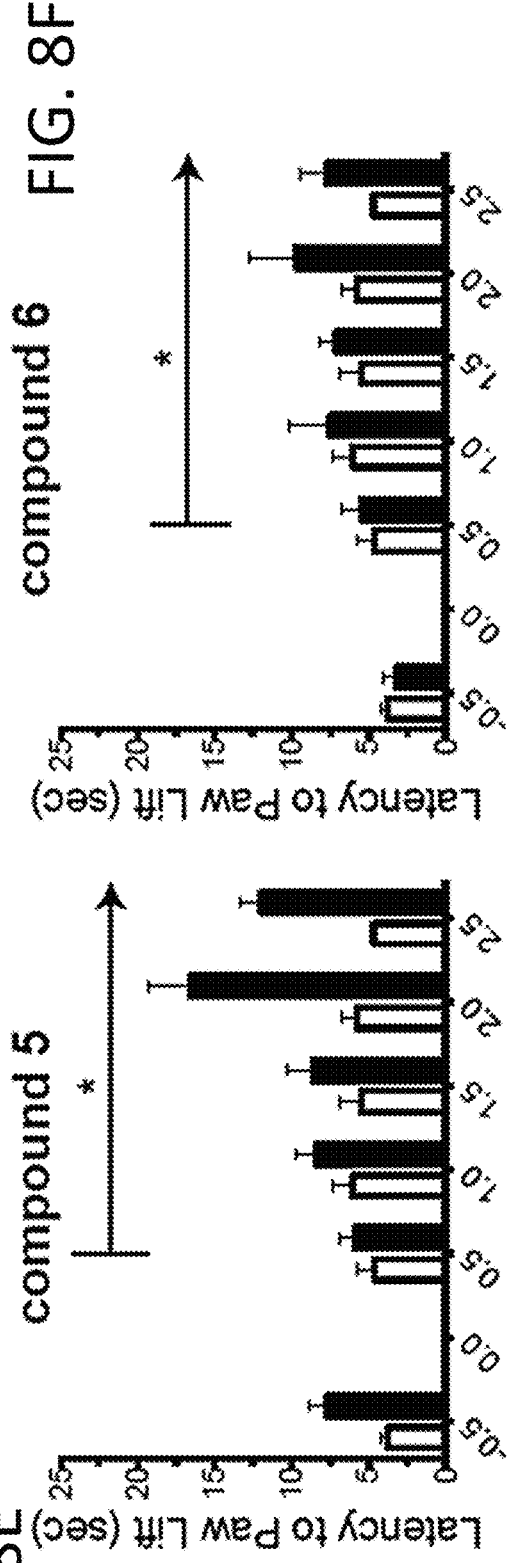
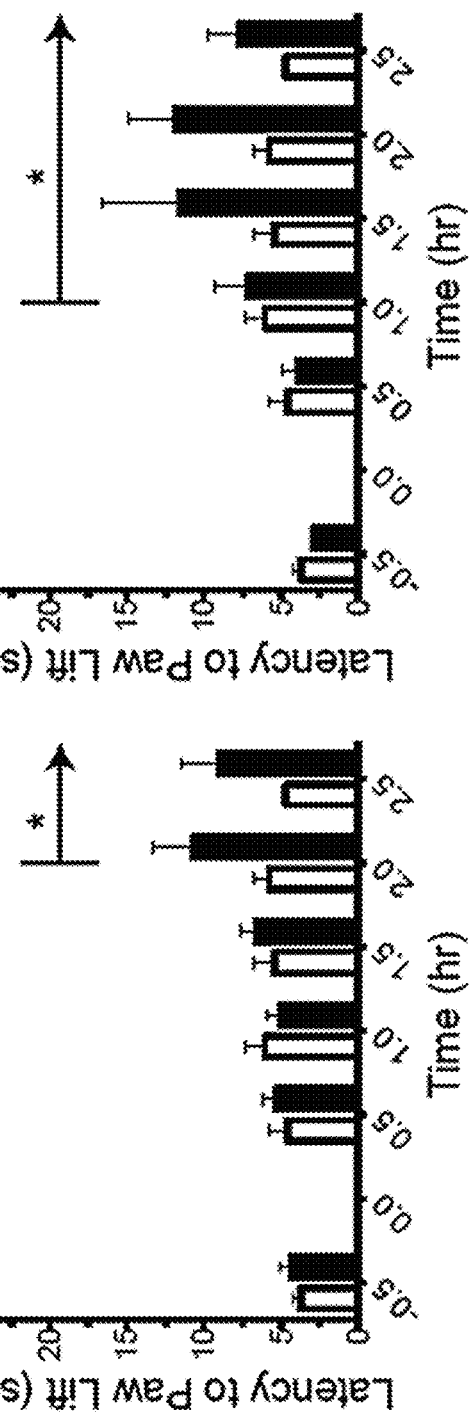
FIG. 8E  FIG. 8F  FIG. 8G  FIG. 8H

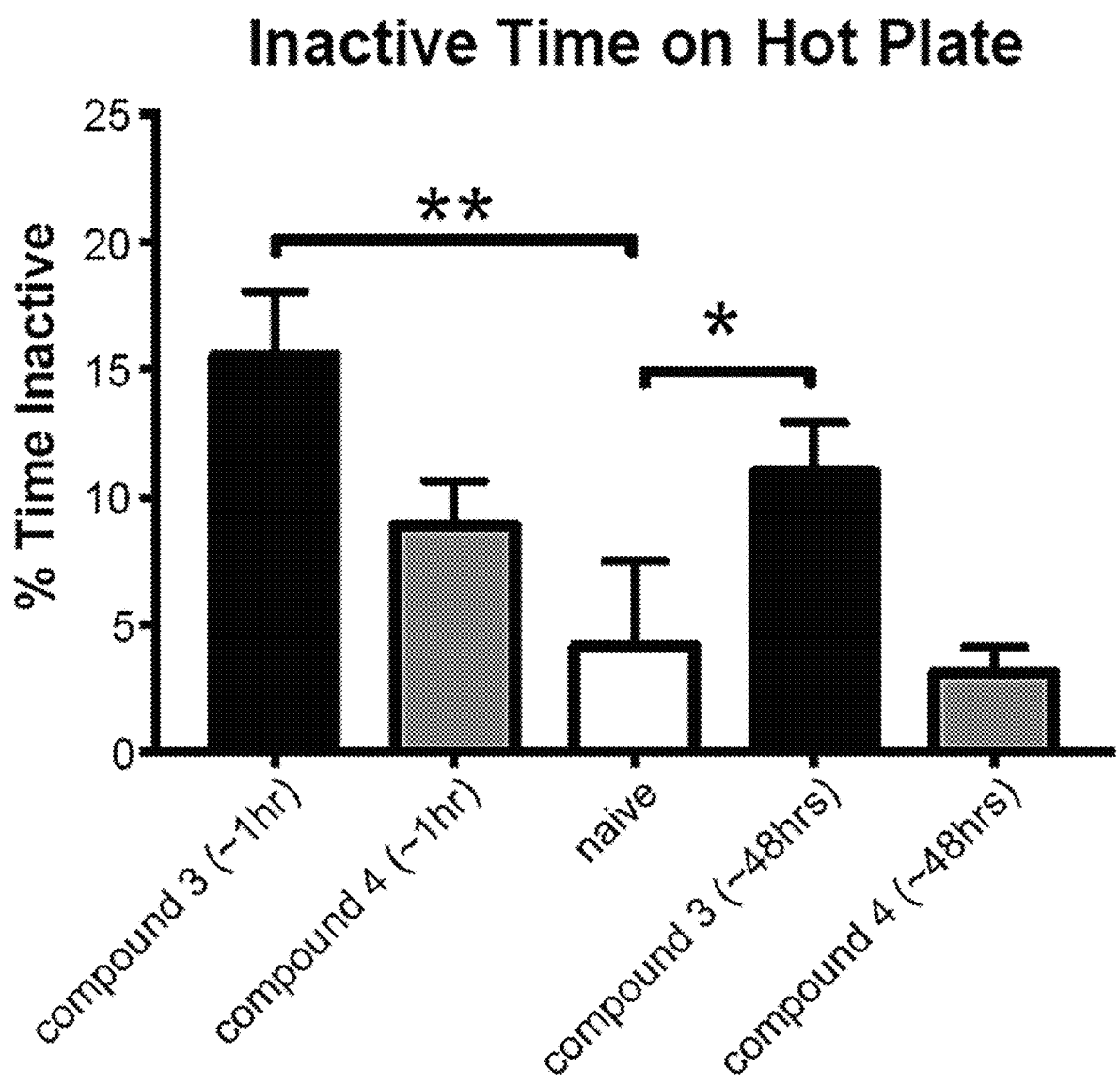

GLYCINE RECEPTOR MODULATORS AND METHODS OF USE

CROSS-REFERENCE TO RELATED APPLICATIONS

This is a divisional of U.S. application Ser. No. 16/631,422, filed Jan. 15, 2020, which is the U.S. National Stage of International Application No. PCT/US2018/042162, filed Jul. 13, 2018, which was published in English under PCT Article 21(2), which application in turn claims the benefit of U.S. Provisional Application No. 62/534,127, filed Jul. 18, 2017 and U.S. Provisional Application No. 62/598,951, filed Dec. 14, 2017, both of which are incorporated herein by reference.

STATEMENT OF GOVERNMENT SUPPORT

This invention was made with government support under NIH R01GM049202, R01GM066358, and R01GM056527 awarded by the National Institutes of Health. The government has certain rights in the invention.

FIELD

This disclosure concerns compounds and methods for modulating the activity of receptors. Embodiments of the disclosed compounds may be useful for treatment of pain, for treatment of opioid addiction, and/or for reduction of side effects attributable to opioid use.

BACKGROUND

The treatment of pain conditions is of great importance in medicine. There is currently a worldwide need for additional pain therapy. "Pain" is defined by the International Association for the Study of Pain (IASP) as "an unpleasant sensory and emotional experience associated with actual or potential tissue damage, or described in terms of such damage" (IASP, Classification of chronic pain, 2.sup.nd Edition, IASP Press (2002), 210). Physiological and psychological factors affect the perception of pain. Some of the relevant pain subtypes are nociceptive pain, inflammatory pain, neuropathic pain, idiopathic pain, phantom pain, allodynia, hyperalgesia, and peripheral neuropathy.

Postsurgical pain (interchangeably termed, post-incisional pain), or pain that occurs after surgery or traumatic injury, is serious and often intractable. Pain is usually localized within the vicinity of the surgical site. Postsurgical pain can have two clinically important aspects, namely resting pain, or pain that occurs when the patient is not moving, and mechanical pain which is exacerbated by movement (coughing/sneezing, getting out of bed, physiotherapy, etc.). Drugs that are used to treat this pain often have a variety of side effects that delay recovery, prolong hospitalization and can have debilitating complications.

The major classes of pharmaceutical drugs used to treat various forms of pain are opioid analgesics, local anesthetics, non-steroidal anti-inflammatory drugs (NSAID), anti-depressants, and cannabinoids. Local anesthetics (e g channel blockers) are administered non-systemically during surgery while the other four classes of drugs, the opioid analgesics, NSAIDs, anti-depressants, and cannabinoids, are typically administered systemically. However, all the major classes of drugs for the treatment of pain are associated with risks of drug tolerance, dependence, or abuse. Analgesic tolerance often leads to hyperalgesia, requiring higher and higher doses of medication. Based on a 2011 report, prescription drugs for pain, or painkillers, kill twice as many people as cocaine and five times as many people as heroin (*Harvard Mental Health Letter*, 27:4-5, 2011).

The analgesic effects of THC are attributed to its potentiation of glycine receptors (Xiong et al. Nat Chem Biol, 2011). The representative compound was identified through the structure determination of the THC binding site and computational screening of a library of drug-like molecules at the binding site where THC is known to modulate glycine receptors. In vitro electrophysiology measurements of GlyR channel functions confirm intended modulations by the representative compound (FIG. 1, 2). In vivo behavior tests in C57BL/6 and CD1 mice validate the analgesic action of the representative compound in response to inflammation (FIG. 4). Many of the adverse effects from drugs of abuse are due to their action on targets other than glycine receptors. For example, THC produces motor impairment and psychosis through modulation of cannabinoid receptors (Pacher et al., Pharmacol Rev, 2006). Therefore, compounds selectively targeting the glycine receptors are advantageous for human use.

SUMMARY

Embodiments of receptor modulators and uses thereof are disclosed. The receptor modulators are compounds having a structure according to formula I, or a stereoisomer, tautomer, or pharmaceutically acceptable salt thereof:

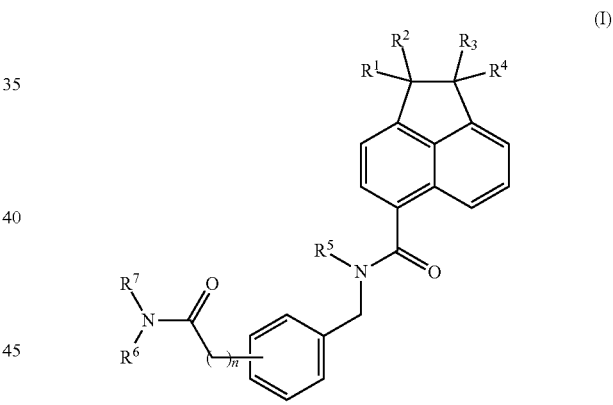

(I)

where $R^1$, $R^2$, $R^3$, and $R^4$ independently are hydrogen, halo, or hydroxy; $R^5$ is hydrogen, halo, $C_1$-$C_{10}$ alkyl, or hydroxy; $R^6$ and $R^7$ independently are hydrogen, halo, hydroxy, $C_1$-$C_{10}$ alkyl, or $C_1$-$C_{10}$ alkyl carboxamide, or $R^6$ and $R^7$ together with the nitrogen to which they are bound form a heterocycloaliphatic or heteroaryl group; and n is 0, 1, 2, or 3.

Embodiments of the disclosed compounds are useful for modulating activity of a receptor, such as glycine receptor (GlyR), reducing pain in a subject, treating opioid addiction in a subject, and/or reducing side effects attributable to opioid use in a subject.

A method of modulating a GlyR, such as a human GlyR, includes contacting the GlyR with an effective amount of a compound as disclosed herein. In some embodiments, the compound enhances or inhibits activity of the GlyR. In certain embodiments, the GlyR is human α1GlyR, α2GlyR, α3GlyR, α1βGlyR, α2βGlyR, α3β3GlyR, or a combination thereof. The GlyR may be contacted in vitro, ex vivo, or in vivo, e.g., by administering the compound or a pharmaceutically acceptable salt thereof to a subject.

A method for reducing pain in a subject includes administering to the subject an effective amount of a compound as disclosed herein. The pain may be inflammatory hypersensitivity, postsurgical pain, pain associated with tissue damage, pain from infection, pain from a neuropathic condition, pain from a skeletal muscular condition, or a combination thereof. A method for treating opioid addiction and/or reducing side effects attributable to opioid use in a subject includes administering to the subject an effective amount of a compound as disclosed herein.

In any or all of the above embodiments, administering the effective amount of the compound to the subject may include administering an amount of a pharmaceutical composition comprising the effective amount of the compound to the subject. In any or all of the above embodiments, the effective amount of the compound may be within a range of from 0.001-100 mg/kg body weight.

In any or all of the above embodiments, the compound and a second therapeutic agent may be co-administered to the subject, wherein the second therapeutic agent is an opioid, nonsteroidal anti-inflammatory drug, COX-2 inhibitor, cannabinoid, antidepressant, local anesthetic, or anti-inflammatory steroid. Co-administration may be performed simultaneously or sequentially in any order. In one embodiment, the compound and the second therapeutic agent are simultaneously administered to the subject in a single pharmaceutical composition. In an independent embodiment, the compound and the second therapeutic agent are administered in separate pharmaceutical compositions by the same or different routes of administration. In any or all of the foregoing embodiments, the second therapeutic agent may be an opioid, and the opioid is administered in an amount that is subclinical by itself.

The foregoing and other objects, features, and advantages of the invention will become more apparent from the following detailed description, which proceeds with reference to the accompanying figures.

BRIEF DESCRIPTION OF THE DRAWINGS

FIGS. 8A-8H are bar graphs showing responses of CD1 mice to the Hargreaves test after application of 0.1 mg/kg of several disclosed compounds (black) or vehicle (white) under CFA-induced hyperalgesic conditions. The assessed compounds were compound 1 (8A), 2 (8B), 3 (8C), 4 (8D), 5 (8E), 6 (8F), 7 (8G), and 8 (8H).

FIG. 9 is a bar graph showing duration of analgesic effects provided by compounds 3 and 4.

DETAILED DESCRIPTION

Figure 1:
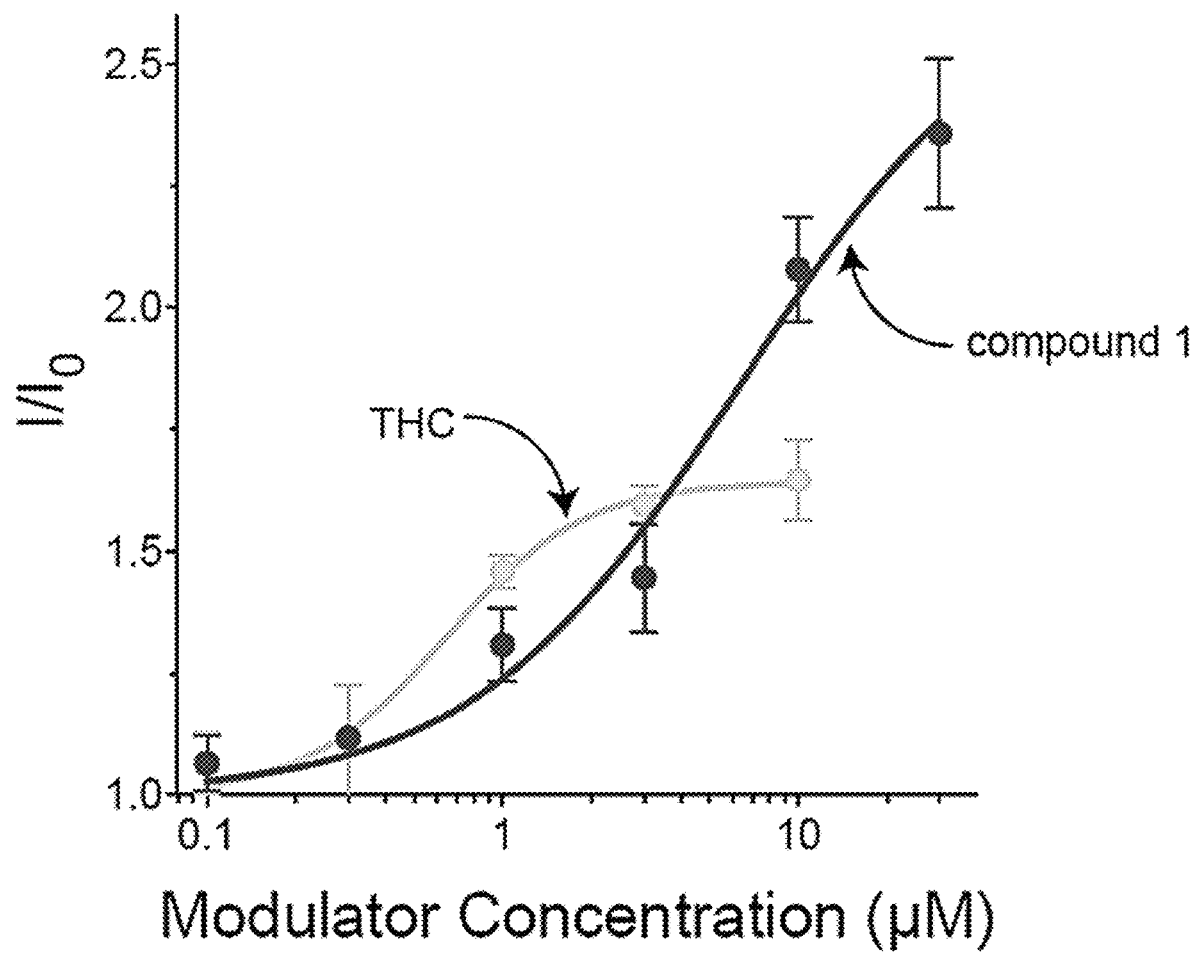
FIG. 1 is a graph showing modulation of human α3GlyR expressed in *Xenopus laevis* oocytes activated by 2% maximal effective concentration of glycine in the presence of a compound as disclosed herein (compound 1).

Embodiments of compounds and methods for modulating the activity of receptors are disclosed. In some embodiments, the disclosed compounds are useful for analgesia, and may be useful for treating opioid addiction and/or reducing side effects attributable to opioid use, e.g., by reducing pain so that opioid dosages may be reduced.

Embodiments of the disclose compounds represent a novel class of receptor modulators for the treatment of pain and/or opioid addiction. In some embodiments, the compounds modulate one or more glycine receptors (GlyR). Certain embodiments of the disclosed compounds have shown profound analgesic effects in treating inflammatory hypersensitivity with no effect on normal nociception. New formulations of this class of modulators with greatly reduced requirement for opioids can be used to eliminate many of the undesirable side effects associated with a high dose of opioids, including drug dependence, tolerance, addiction, sedation, and nausea. The disclosed class of compounds is not previously known to contribute to analgesia, either alone or in combination with opioids.

I. DEFINITIONS AND ABBREVIATIONS

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, temperatures, times, and so forth, as used in the specification or claims are to be understood as being modified by the term "about." As used herein, the term "about" or the symbol "~" refers to a ±10% variation from the nominal value unless otherwise indicated or inferred. Accordingly, unless otherwise implicitly or explicitly indicated, or unless the context is properly understood by a person of ordinary skill in the art to have a more definitive construction, the numerical parameters set forth are approximations that may depend on the desired properties sought and/or limits of detection under standard test conditions/methods as known to those of ordinary skill in the art. When directly and explicitly distinguishing embodiments from discussed prior art, the embodiment numbers are not approximates unless the word "about" is recited.

At various places in the present specification, substituents are disclosed in groups or in ranges. It is specifically intended that the description include each and every individual subcombination of the members of such groups and ranges. For example, the term "C1-C5 alkyl" is specifically intended to individually disclose C1, C2, C3, C4, C5, C1-C5, C1-C4, C1-C3, C1-C2, C2-C5, C2-C4, C2-C3, C3-C5, C3-C4, and C4-C5 alkyl.

Aliphatic: A substantially hydrocarbon-based compound, or a radical thereof (e.g., $C_6H_{13}$, for a hexane radical), including alkanes, alkenes, alkynes, including cyclic versions thereof, and further including straight- and branched-chain arrangements, and all stereo and position isomers as well. Unless expressly stated otherwise, an aliphatic group contains from one to twenty-five carbon atoms; for example, from one to fifteen, from one to ten, from one to six, or from one to four carbon atoms. Unless expressly referred to as an "unsubstituted aliphatic," an aliphatic group can either be unsubstituted or substituted. An aliphatic group can be substituted with one or more substituents (up to two substituents for each methylene carbon in an aliphatic chain, or up to one substituent for each carbon of a —C═C— double bond in an aliphatic chain, or up to one substituent for a carbon of a terminal methine group). Exemplary substituents include, but are not limited to, alkyl, alkenyl, alkynyl, alkoxy, alkylamino, alkylthio, acyl, aldehyde, amide, amino, aminoalkyl, aryl, arylalkyl, carboxyl, cyano, cycloalkyl, dialkylamino, halo, haloaliphatic, heteroaliphatic, heteroaryl, heterocycloaliphatic, hydroxyl, oxo, sulfonamide, sulfhydryl, thioalkoxy, or other functionality.

Alkyl: A hydrocarbon group having a saturated carbon chain. The chain may be cyclic, branched or unbranched. Examples, without limitation, of alkyl groups include methyl, ethyl, propyl (e.g., n-propyl and isopropyl), butyl (e.g., n-butyl, isobutyl, sec-butyl, tert-butyl), pentyl, hexyl, heptyl, octyl, nonyl and decyl. Unless expressly referred to as an "unsubstituted alkyl," an alkyl group can either be unsubstituted or substituted.

Carboxamide: A group having a general structure —C(O)NR'R", wherein R' and R" independently are hydrogen or alkyl. An alkyl carboxamide group has a general structure —RC(O)NR'R", wherein R is an alkyl group and R' and R" independently are hydrogen or alkyl.

Effective amount (or dose): An amount sufficient to effect a change, such as a change in activity or function of a glycine receptor.

Excipient: A physiologically inert substance that is used as an additive in a pharmaceutical composition. As used herein, an excipient may be incorporated within particles of a pharmaceutical composition, or it may be physically mixed with particles of a pharmaceutical composition. An excipient can be used, for example, to dilute an active agent and/or to modify properties of a pharmaceutical composition. Examples of excipients include but are not limited to polyvinylpyrrolidone (PVP), tocopheryl polyethylene glycol 1000 succinate (also known as vitamin E TPGS, or TPGS), dipalmitoyl phosphatidyl choline (DPPC), trehalose, sodium bicarbonate, glycine, sodium citrate, and lactose.

Glycine receptor (GlyR): The receptor for the amino acid neurotransmitter glycine. GlyR is an ionotropic receptor that produces its effects through a chloride current. It is an inhibitory receptor that is found throughout the central nervous system. This receptor has important roles in a variety of physiological processes, such as for mediating inhibitory neurotransmission in the spinal cord and brain stem. GlyR can be activated by glycine, 0-alanine and taurine, and can be selectively blocked by the high-affinity competitive antagonist strychnine Caffeine is an antagonist of this receptor. The glycine receptor (GlyR) transmembrane domain (TMD) alone, without the extracellular and intracellular domains, spontaneously forms Cr-conducting channels (Structure, 21:1897-904, 2013). Exemplary sequences for the GlyR are shown in GENBANK Accession Nos. NM_001146040.1 (NP_001139512.1), and NM_000171.3. (NP_000162.2), all incorporated by reference herein as available on Dec. 9, 2013. The TMD of the GlyR α1 and α3 subunits harbors a novel cannabinoid-binding site that mediates marijuana's analgesic effects but not the psychoactive effects (*Nature Chemical Biology*, 7:296-303, 2011; *Journal of Experimental Medicine*, 209:1121-34, 2012). The human body has few or no glycine receptors in the peripheral nervous system.

Halogen (halo): The term halogen includes fluorine, chlorine, bromine, and iodine. Similarly, the term halo includes fluoro, chloro, bromo, and iodo.

Heteroaliphatic: An aliphatic compound or group having at least one heteroatom, i.e., one or more carbon atoms has been replaced with an atom having at least one lone pair of electrons, typically nitrogen, oxygen, phosphorus, silicon, or sulfur. Heteroaliphatic compounds or groups may be substituted or unsubstituted, branched or unbranched, cyclic or acyclic, and include "heterocycle", "heterocyclyl", "heterocycloaliphatic", or "heterocyclic" groups.

Heteroaryl: An aromatic compound or group having at least one heteroatom, i.e., one or more carbon atoms in the ring has been replaced with an atom having at least one lone pair of electrons, typically nitrogen, oxygen, phosphorus, silicon, or sulfur.

Nociception: Neural process of encoding and processing a noxious stimulus.

Nociceptor: A receptor at the end of a sensory neuron's axon, which responds to damaging or potentially damaging stimuli. Nociceptors include thermal, mechanical, chemical, sleeping/silent, and polymodal nociceptors.

Pain: An unpleasant sensory and emotional experience associated with actual or potential tissue damage, or described in terms of such damage (IASP, Classification of chronic pain, second Edition, IASP Press (2002), 210). In particular examples of this disclosed methods the pain is medicated by nociceptors. Pain includes postsurgical pain, pain associates with tissue damage, pain from inflammation, pain from infection (shingles), pain from neuropathic conditions, and pain from skeletal muscular conditions.

Pharmaceutically acceptable: A substance that can be taken into a subject without significant adverse toxicological effects on the subject. The term "pharmaceutically acceptable form" means any pharmaceutically acceptable derivative or variation, such as stereoisomers, stereoisomer mixtures, enantiomers, solvates, hydrates, isomorphs, polymorphs, pseudomorphs, neutral forms, salt forms, and prodrug agents.

Pharmaceutically acceptable carrier: The pharmaceutically acceptable carriers (vehicles) useful in this disclosure are conventional. Remington: The Science and Practice of Pharmacy, The University of the Sciences in Philadelphia, Editor, Lippincott, Williams, & Wilkins, Philadelphia, PA, 21$^{st}$ Edition (2005), describes compositions and formulations suitable for pharmaceutical delivery of one or more therapeutic compositions and additional pharmaceutical agents. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In some examples, the pharmaceutically acceptable carrier is a non-naturally occurring or synthetic carrier. The carrier also can be formulated in a unit-dosage form that carries a preselected therapeutic dosage of the active agent, for example in a pill, vial, bottle, or syringe.

Pharmaceutically acceptable salt: A biologically compatible salt of a compound that can be used as a drug, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. Pharmaceutically acceptable acid addition salts are those salts that retain the biological effectiveness of the free bases while formed by acid partners that are not biologically or otherwise undesirable, e.g., inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, benzene sulfonic acid (besylate), cinnamic acid, mandelic acid, methanesulfonic acid, ethanesulfonic acid, p-toluenesulfonic acid, salicylic acid and the like. Pharmaceutically acceptable base addition salts include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19, which is incorporated herein by reference.)

Stereoisomers: Compounds described herein can contain an asymmetric atom (also referred as a chiral center) and some of the compounds can contain two or more asymmetric atoms or centers, which can thus give rise to stereoisomers. Stereoisomers have the same molecular formula and sequence of bonded atoms, but differ only in the three-dimensional orientation of the atoms in space. Stereoisomers that are not mirror images of one another are termed "diastereomers" and those that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−) isomers respectively). A chiral compound can exist as either individual enantiomer or as a mixture thereof. A mixture containing equal proportions of the enantiomers is called a "racemic mixture." In some embodiments, optical isomers can be obtained in enantiomerically enriched or pure form by standard procedures known to those skilled in the art, which include, for example, chiral separation, diastereomeric salt formation, kinetic resolution, and asymmetric synthesis. E/Z isomers are isomers that differ in the stereochemistry of a double bond. An E isomer (from entgegen, the German word for "opposite") has a trans-configuration at the double bond, in which the two groups of highest priority are on opposite sides of the double bond. A Z isomer (from zusammen, the German word for "together") has a cis-configuration at the double bond, in which the two groups of highest priority are on the same side of the double bond. It also should be understood that the compounds of the present teachings encompass all possible regioisomers in pure form and mixtures thereof. In some embodiments, the preparation of the present compounds can include separating such isomers using standard separation procedures known to those skilled in the art, for example, by using one or more of column chromatography, thin-layer chromatography, simulated moving-bed chromatography, and high-performance liquid chromatography. However, mixtures of regioisomers can be used similarly to the uses of each individual regioisomer of the present teachings as described herein and/or known by a skilled artisan. It is specifically contemplated that the depiction of one regioisomer includes any other regioisomers and any regioisomeric mixtures unless specifically stated otherwise.

Subclinical/subtherapeutic dose: A dose that is too low to produce a therapeutic effect in a subject, e.g., too low to treat the disease for which it is administered and/or too low to have a therapeutic effect. For example, a subclinical dose of an opioid is insufficient to fully ameliorate pain in a subject and/or to reduce pain to a tolerable level in the subject.

Tautomers: Constitutional isomers of organic compounds that differ only in the position of the protons and electrons, and are interconvertible by migration of a hydrogen atom. Tautomers ordinarily exist together in equilibrium.

Therapeutic agent: An agent that provides a beneficial, or therapeutic, effect to a subject or a given percentage of subjects.

Therapeutically effective amount (or dose): An amount sufficient to provide a beneficial, or therapeutic, effect to a subject or a given percentage of subjects.

Therapeutic time window: The length of time during which an effective, or therapeutic dose, of a compound remains therapeutically effective in vivo.

Treating or treatment: With respect to disease, either term includes (1) preventing the disease, e.g., causing the clinical symptoms of the disease not to develop in an animal that may be exposed to or predisposed to the disease but does not yet experience or display symptoms of the disease, (2) inhibiting the disease, e.g., arresting the development of the disease or its clinical symptoms, or (3) relieving the disease, e.g., causing regression of the disease or its clinical symptoms.

II. RECEPTOR MODULATORS

In some embodiments, a receptor modulator is a compound having a structure according to formula I, or a stereoisomer, tautomer, or pharmaceutically acceptable salt thereof:

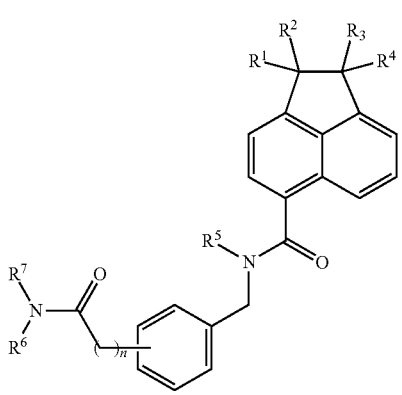

(I)

where $R^1$, $R^2$, $R^3$, and $R^4$ independently are hydrogen, halo, or hydroxy; $R^5$ is hydrogen, halo, $C_1$-$C_{10}$ alkyl, or hydroxy; $R^6$ and $R^7$ independently are hydrogen, halo, hydroxy, $C_1$-$C_{10}$ alkyl, or $C_1$-$C_{10}$ alkyl carboxamide, or $R^6$ and $R^7$ together with the nitrogen to which they are bound form an optionally substituted heterocycloaliphatic or heteroaryl group; and n is 0, 1, 2, or 3.

In certain embodiments, the compound has a structure according to formula II or formula

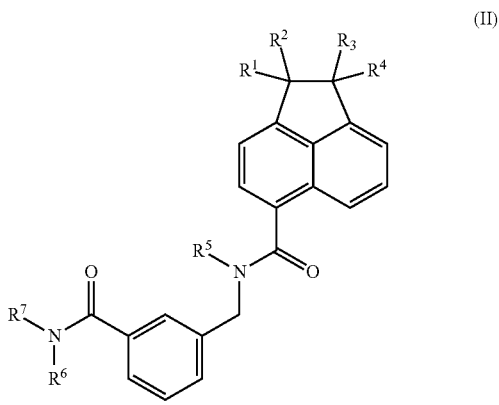

(II)

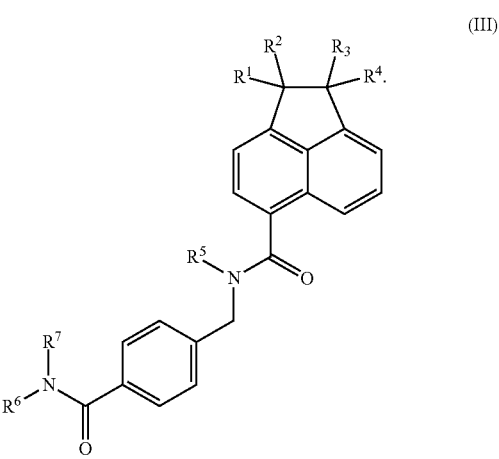

(III)

In any or all of the above embodiments, $R^1$-$R^4$ may be hydrogen.

In any or all of the above embodiments, $R^5$ may be hydrogen, halo, $C_1$-$C_8$ alkyl, or hydroxy. In certain embodiments, $R^5$ is hydrogen. In an independent embodiment, $R^5$ is $C_1$-$C_3$ alkyl. In any or all of the above embodiments, $R^6$ and $R^7$ independently may be hydrogen, halo, methyl, ethyl, propyl, isopropyl, hydroxy, or —$CH_2C(O)NH_2$, or $R^6$ and $R^7$ together with the nitrogen to which they are bound may form a substituted or unsubstituted piperidinyl or piperazinyl group. In one embodiment, $R^6$ and $R^7$ are hydrogen. In an independent embodiment, $R^6$ and $R^7$ are methyl. In another independent embodiment, one of $R^6$ and $R^7$ is hydrogen, and the other of $R^6$ and $R^7$ is $C_1$-$C_3$ alkyl. In another independent embodiment, one of $R^6$ and $R^7$ is hydrogen, and the other of $R^6$ and $R^7$ is —$CH_2C(O)NH_2$. In yet another independent embodiment, $R^6$ and $R^7$ together with the nitrogen to which they are bound form a piperidinyl group. In still another independent embodiment, $R^6$ and $R^7$ together with the nitrogen to which they are bound form a piperazinyl group, such as a substituted piperazinyl group, e.g., a 3-oxopiperazinyl group.

Several representative compounds according to formula I are shown in Table 1.

TABLE 1

Representative compounds.

| Short Name/ ZINC ID | IUPAC Name | Structure |
| --- | --- | --- |
| compound 1 ZINC025333975 | N-[(3-carbamoylphenyl)-methyl]-1,2-dihydroacenaphthylene-5-carboxamide | 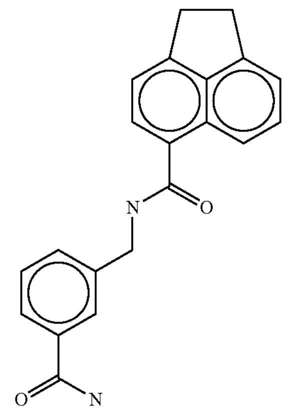 |
| compound 2 ZINC027158519 | N-{[4-(piperidine-1-carbonyl)phenyl]methyl}-1,2-dihydroacenaphthylene-5-carboxamide | 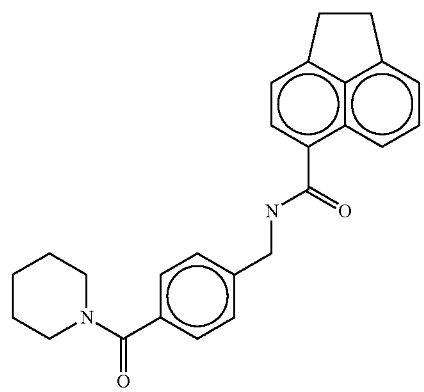 |
| compound 3 ZINC047218430 | N-({4-[(carbamoylmethyl)-carbamoyl]phenyl}methyl)-1,2-dihydroacenaphthylene-5-carboxamide | 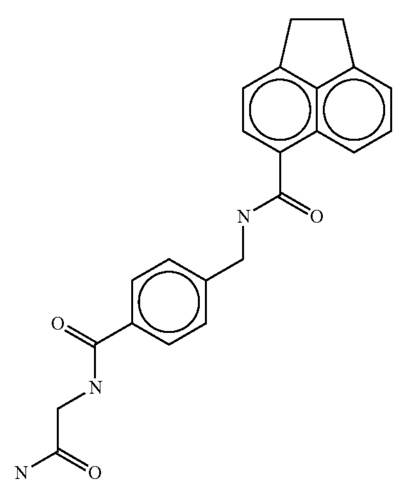 |

TABLE 1-continued

Representative compounds.

| Short Name/ ZINC ID | IUPAC Name | Structure |
| --- | --- | --- |
| compound 4 ZINC043773099 | N-[[3-(dimethylcarbamoyl)- phenyl]methyl]-1,2- dihydroacenaphthylene-5-carboxamide | 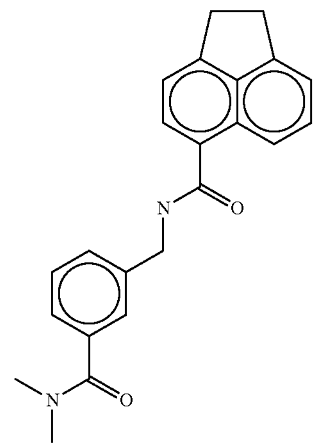 |
| compound 5 ZINC046561815 | N-[(4-carbamoylphenyl)-methyl]-1,2- dihydroacenaphthylene-5-carboxamide | 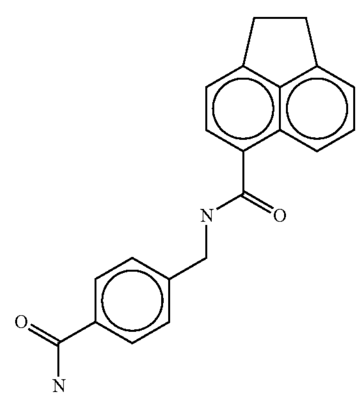 |
| compound 6 ZINC053991769 | N-{[4-(3-oxopiperazine-1- carbonyl)phenyl]methyl}-1,2- dihydroacenaphthylene-5-carboxamide | 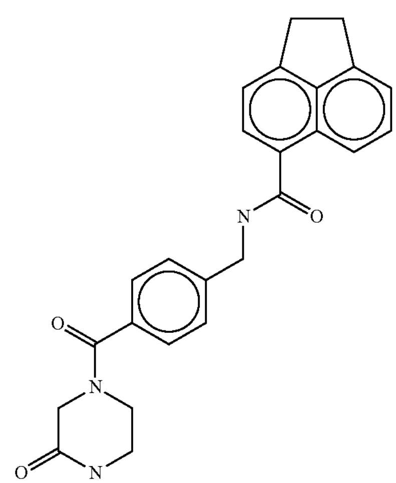 |

TABLE 1-continued

Representative compounds.

| Short Name/ ZINC ID | IUPAC Name | Structure |
| --- | --- | --- |
| compound 7 ZINC476467271 | N-{[4-(dimethylcarbamoyl)-phenyl]methyl}-N-ethyl-1,2-dihydroacenaphthylene-5-carboxamide | 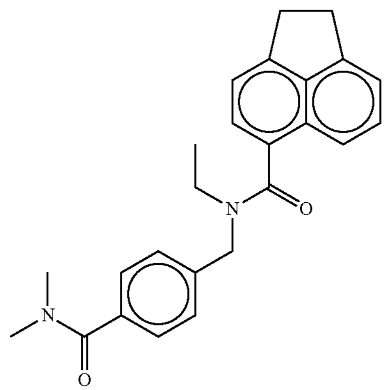 |
| compound 8 ZINC047141882 | N-{[4-(ethylcarbamoyl)-phenyl]methyl}-1,2-dihydroacenaphthylene-5-carboxamide | 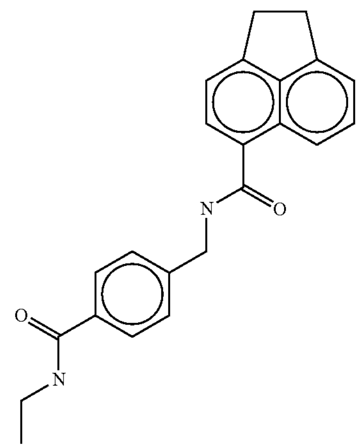 |

III. PHARMACEUTICAL COMPOSITIONS

Embodiments of the disclosed pharmaceutical compositions include a compound according to formula I, or a stereoisomer, tautomer, or pharmaceutically acceptable salt thereof and at least one pharmaceutically acceptable additive such as pharmaceutically acceptable carriers, thickeners, diluents, buffers, preservatives, surface active agents and the like in addition to the molecule of choice. Pharmaceutical compositions can also include one or more additional active ingredients such as anti-arrhythmia agents, anti-hypertension agents, antimicrobial agents, anti-inflammatory agents, anesthetics, and the like. The pharmaceutically acceptable carriers useful for these formulations are conventional. Remington's Pharmaceutical Sciences, by E. W. Martin, Mack Publishing Co., Easton, PA, 19th Edition (1995), for example, describes compositions and formulations suitable for pharmaceutical delivery of the compounds herein disclosed.

The pharmaceutical compositions may be in a dosage unit form such as an injectable fluid, an oral delivery fluid (e.g., a solution or suspension), a nasal delivery fluid (e.g., for delivery as an aerosol or vapor), a semisolid form (e.g., a topical cream), or a solid form such as powder, pill, tablet, or capsule forms.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The compounds (hereinafter referred to as "the agents") disclosed herein can be administered to subjects by a variety of routes, including by intramuscular, subcutaneous, intravenous, intra-arterial, intra-articular, intraperitoneal, intrathecal, intracerebroventricular, parenteral, oral, rectal, intranasal, intrapulmonary, transdermal, or topical routes. In other alternative embodiments, the agents can be administered ex vivo by direct exposure to cells, tissues or organs originating from a subject.

To formulate the pharmaceutical compositions, the agents can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, isotonizing agents (for example, sodium chloride, mannitol, sorbitol), adsorption inhibitors (for example, Tween® 80 polyethylene sorbitol ester or Miglyol® 812 triglycerides), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, NJ), Freund's adjuvant, MPL™ (3-O-deacylated monophosphoryl lipid A; Corixa, Hamilton, IN) and IL-12 (Genetics Institute, Cambridge, MA), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The agents can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The agents can be combined with the base or vehicle according to a variety of methods, and release of the agents can be by diffusion, disintegration of the vehicle, or associated formation of water channels. In some circumstances, the agent is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the agents can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the agents can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly (epsilon-caprolactone), poly(epsilon-caprolactone-CO-lactic acid), poly(epsilon.-caprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the agent can be delivered to a subject in a manner consistent with conventional methodologies associated with management of the disorder for which treatment or prevention is sought. In accordance with the disclosure herein, a prophylactically or therapeutically effective amount of the agent is administered to a subject in need of such treatment for a time and under conditions sufficient to prevent, inhibit, and/or ameliorate a selected condition or one or more symptom(s) thereof.

The administration of the agents can be for either prophylactic or therapeutic purpose. When provided prophylactically, the agents are provided in advance of any symptom. The prophylactic administration of the agents serves to prevent or ameliorate any subsequent pain or opioid withdrawal symptom. When provided therapeutically, the agents are provided at (or shortly after) the onset of an undesirable symptom, e.g., pain or opioid withdrawal symptom.

For prophylactic and therapeutic purposes, the agents can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosages of the agents can be provided as repeated doses within a prolonged prophylaxis or treatment regimen that will yield clinically significant results to alleviate one or more symptoms or detectable conditions associated with a targeted condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to elicit a desired immune response or alleviate one or more symptoms of a targeted disease). In alternative embodiments, an effective amount or effective dose of the agents may simply inhibit or enhance one or more selected biological activities correlated with a disease or condition, as set forth herein, for either therapeutic or diagnostic purposes.

The actual dosages of the agents will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the agent for eliciting the desired activity or biological response in the subject. Dosage regimens can be adjusted to provide an optimum prophylactic or therapeutic response. A therapeutically effective amount is also one in which any toxic or detrimental side effects of the agent is outweighed in clinical terms by therapeutically beneficial effects. A non-limiting range for a therapeutically effective amount of an agent within the methods and formulations of the disclosure is 0.001 mg/kg body weight to 100 mg/kg body weight, such as 0.01 mg/kg body weight to 20 mg/kg body weight, 0.01 mg/kg body weight to 10 mg/kg body weight 0.05 mg/kg to 5 mg/kg body weight, or 0.2 mg/kg to 2 mg/kg body weight. Dosage can be varied by the attending clinician to maintain a desired concentration at a target site (for example, systemic circulation). Higher or lower concentrations can be selected based on the mode of delivery, for example, trans-epidermal or oral delivery versus intravenous or subcutaneous delivery. Dosage can also be adjusted based on the release rate of the administered formulation, for example, of sustained release oral versus injected particulate or transdermal delivery formulations, and so forth.

IV. METHODS OF USE

Embodiments of the disclosed compounds may be used for reducing pain in a subject, for treating opioid addiction, for reducing side effects attributable to opioid use in a subject, and/or for modulating a receptor, such as a glycine receptor (GlyR). Certain embodiments of the disclosed compounds can be co-administered with an opioid to ameliorate pain in a subject with greatly reduced opioid dosage, thereby eliminating undesirable side effects associated with high doses of opioids, including drug dependence, tolerance, addiction, sedation, opioid-induced constipation, and/or nausea. Some embodiments of the disclosed compounds modulate specific GlyR subtypes by binding to an interfacial site within the transmembrane domain of the receptor. This same site has previously been shown to be responsible for GlyR modulation by tetrahydrocannabinol (THC), the primary psychoactive and analgesic component of *cannabis*. THC binding to GlyR at this site is known to produce an analgesic effect in mammals. In addition, certain embodiments of the disclosed receptor modulators demonstrate analgesic synergy with opioids, greatly reducing the dosage of opioids such as morphine required to achieve the same pharmacological effects.

Embodiments of a method for modulating a GlyR including contacting the GlyR with an effective amount of a compound having a structure according to formula I, or a stereoisomer, tautomer, or pharmaceutically acceptable salt thereof. Contacting the GlyR with the effective amount of the compound may enhance or inhibit activity of the GlyR. In some embodiments, the GlyR is a human GlyR. Human GlyRs include α1GlyR, α2βGlyR, α3GlyR, α1βGlyR, α2βGlyR, α3βGlyR, and combinations thereof. In one embodiment, the GlyR is contacted in vitro. In another embodiment, the compound is administered ex vivo by direct exposure to cells, tissues or organs originating from a subject. In an independent embodiment, the GlyR is contacted in vivo. The GlyR may be contacted in vivo by administering the effective amount of the compound or pharmaceutically acceptable salt thereof to a subject, such as a human.

Embodiments of a method for reducing pain in a subject include administering to the subject an effective amount of a compound having a structure according to formula I, or a stereoisomer, tautomer, or pharmaceutically acceptable salt thereof. The pain may be any type of pain including, but not limited to, inflammatory hypersensitivity, postsurgical pain, pain associated with tissue damage, pain from infection, pain from a neuropathic condition, pain from a skeletal muscular condition, or any combination thereof. Embodiments of a method for treating opioid addiction and/or reducing side effects attributable to opioid use in a subject include administering to the subject an effective amount of a compound having a structure according to formula I, or a stereoisomer, tautomer, or pharmaceutically acceptable salt thereof.

In any or all of the above embodiments, administering the effective amount of the compound according to formula I to a subject may comprise administering an amount of a pharmaceutical composition comprising the effective amount of the compound to the subject. Administration may be by any suitable route including by intramuscular, subcutaneous, intravenous, intra-arterial, intra-articular, intraperitoneal, intrathecal, intracerebroventricular, parenteral, oral, rectal, intranasal, intrapulmonary, transdermal, or topical routes. In any or all of the above embodiments, the effective amount of the compound may be within a range of from 0.001 mg/kg body weight to 100 mg/kg body weight, such as 0.01 mg/kg body weight to 20 mg/kg body weight, 0.01 mg/kg body weight to 10 mg/kg body weight 0.05 mg/kg to 5 mg/kg body weight, or 0.2 mg/kg to 2 mg/kg body weight.

In certain embodiments, administration of the compound according to formula I may be sufficient to modulate a GlyR, reduce pain, and/or reduce or treat opioid addiction in a subject. In other embodiments, it may be beneficial to administer the compound according to formula I in combination with a second therapeutic agent to the subject.

Thus, in any or all of the above embodiments, the compound may be co-administered with a second therapeutic agent to a subject. In some embodiments, the second therapeutic agent is an opioid, analgesic, nonsteroidal anti-inflammatory drug (NSAID), COX-2 inhibitor, cannabinoid, antidepressant, local anesthetic, or anti-inflammatory steroid, or any combination thereof. Opioids include heroin, fentanyl, oxycodone, hydrocodone, hydromorphone, codeine, morphine, meperidine, methadone, and naloxone, among others. Analgesics include opioid and non-opioid pain relievers, such as morphine, fentanyl, hydromorphone, oxycodone, codeine, acetaminophen, hydrocodone, buprenorphine, tramadol, venlafaxine, flupirtine, meperidine, pentazocine, dextromoramide, and dipipanone, among others. NSAIDs include aspirin, ibuprofen, ketoprofen, piroxicam, and COX-2 inhibitors, among others. COX-2 inhibitors include rofecoxib, celecoxib, tilmacoxib, cimicoxib, mavacoxib, firocoxib, valdecoxib, apricoxib, robenacoxib, flumizole, and anitrazafen, among others. Cannabinoids include cannabigerol (CBG), $\Delta^9$-tetrahydrocannabinol (THC), cannabidiol (CBD), cannabigerivarin (CBGV), tetrahydrocannabivarin, (THCV), cannabidivarin (CBDV), and cannabichromevarin (CBCV), among others. Antidepressants include selective serotonin reuptake inhibitors (SSRIs, e.g., citalopram, escitalopram, fluoxetine, fluvoxamine, paroxetine, and sertraline), serotonin-norepinephrine reuptake inhibitors (SNRIs, e.g., desvenlafaxine, duloxetine, venlafaxine, milnacipran, and levomilnacipran), tricyclic antidepressants (TCAs, e.g., amitriptyline, desipramine, doxepine, imipramine, nortriptyline, amoxapine, clomipramine, maprotiline, trimipramine, and protriptyline), monoamine oxidase inhibitors (MAOIs, e.g., phenelzine, selegiline, and tranylcypromine), as well as atypical antidepressants (e.g., bupropion, mirtazapine, mefazodone, trazodone, vilazodone, and vortioxetine). Local anesthetics include lidocaine, mepivacaine, prilocaine, bupivacaine, etidocaine, ropivacaine, levobupivacaine, cocaine, procaine, tetracaine, chloroprocaine, and benzocaine, among others. Anti-inflammatory steroids include betamethasone, prednisone, dexamethasone, cortisone, hydrocortisone, methylprednisolone, and prednisolone, among others.

Co-administration can be performed simultaneously/concurrently or sequentially in any order. When administered simultaneously, the compound according to formula I and the second therapeutic agent may be administered to the subject in a single pharmaceutical composition. Alternatively, the compound and second therapeutic agent may be administered simultaneously in separate pharmaceutical compositions, e.g., as two oral dosage forms taken together.

When administered sequentially, the interval between administration of the compound according to formula I and the second therapeutic agent may range from one second to several days, such as a time interval ranging from one second to several hours, e.g., from one second to 12 hours, from one second to 8 hours, from one second to 6 hours, or from one second to 4 hours. In certain embodiments, the compound according to formula I is administered at any time within a therapeutic time window of the second therapeutic agent. For instance, if the therapeutic time window is 8 hours, the compound according to formula I may be administered within 8 hours of administering a dose of the second therapeutic agent, i.e., within a time interval of from 8 hours prior to administering the second therapeutic agent to 8 hours after administering the second therapeutic agent. When administering sequentially, the compound and the second therapeutic agent may be administered in separate pharmaceutical compositions by the same or different routes of administration.

In some embodiments, a compound according to formula I is co-administered with an opioid to treat opioid addiction and/or reduce side effects attributable to opioid use in a subject. In certain embodiments, administering the compound according to formula I allows a reduction in dosage of the opioid. Thus, the opioid may be administered to the subject in a subclinical or subtherapeutic amount. Advantageously, some embodiments of the disclosed compounds act synergistically with an opioid to further decrease pain in the subject, thereby providing a therapeutic effect that is greater than the benefit that would be expected from either agent alone and even greater than an expected additive benefit of administering both agents to the subject. Co-administration of the compound according to formula I and the opioid may include gradually tapering the opioid dosage over a period of time, thereby further ameliorating undesirable opioid side effects and/or gradually weaning a subject off of the opioid.

V. EXAMPLES

Example 1

In Vitro Modulation of Glycine Receptors

A compound according to formula (II) wherein $R^1$-$R^7$ are hydrogen and n=0 (compound 1) was used as a representative drug.

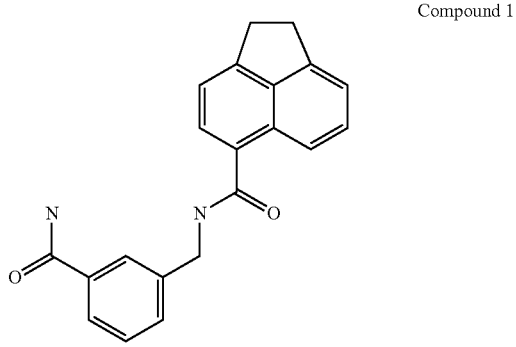 [SMILES: NC(=O)c1cccc(CNC(=O)c2ccc3c4c(cccc24)CC3)c1]

Compound 1

In vitro functional electrophysiology measurements (Current protocols in neuroscience, 6.12:1-20, 2001) demonstrated that compound 1 modulated human GlyRs. FIG. 1 shows the modulation (140) of human α3GlyR expressed in *Xenopus laevis* oocytes activated by 2% maximal effective concentration of glycine. $I/I_o$ is calculated as the ratio of the current measured in the presence (I) and absence ($I_o$) of compound 1 or THC at the indicated concentrations. Error bars designate the standard error of the mean (n≥4).

Figure 2A:
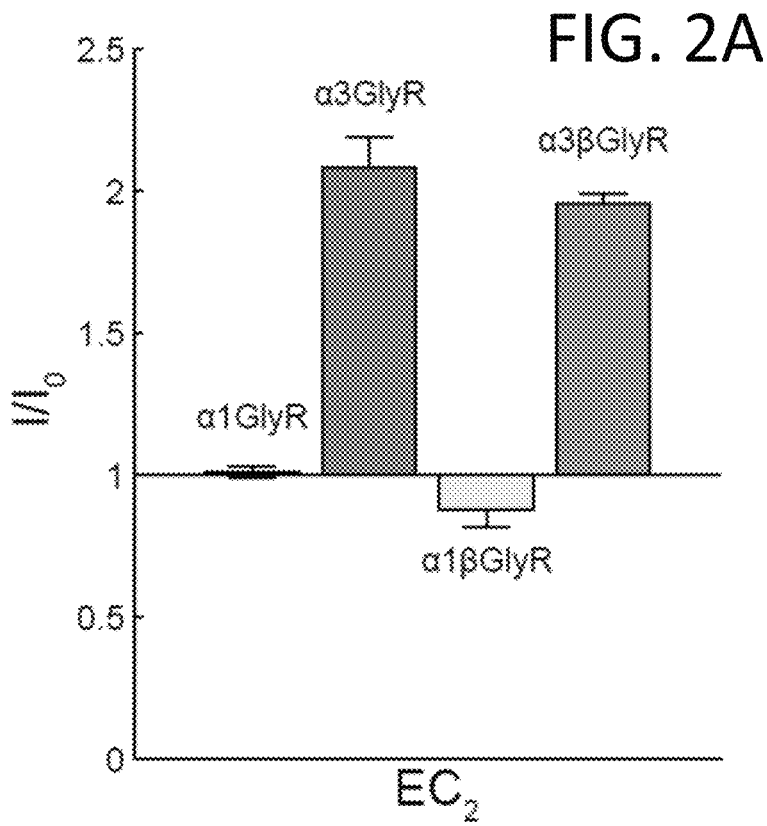
FIGS. 2A and 2B are bar graphs showing modulation of human GlyR subtypes expressed in *Xenopus laevis* oocytes activated by 2% (FIG. 2A) and 20% (FIG. 2B) maximal effective concentration of glycine in the presence of compound 1.
Figure 2B:
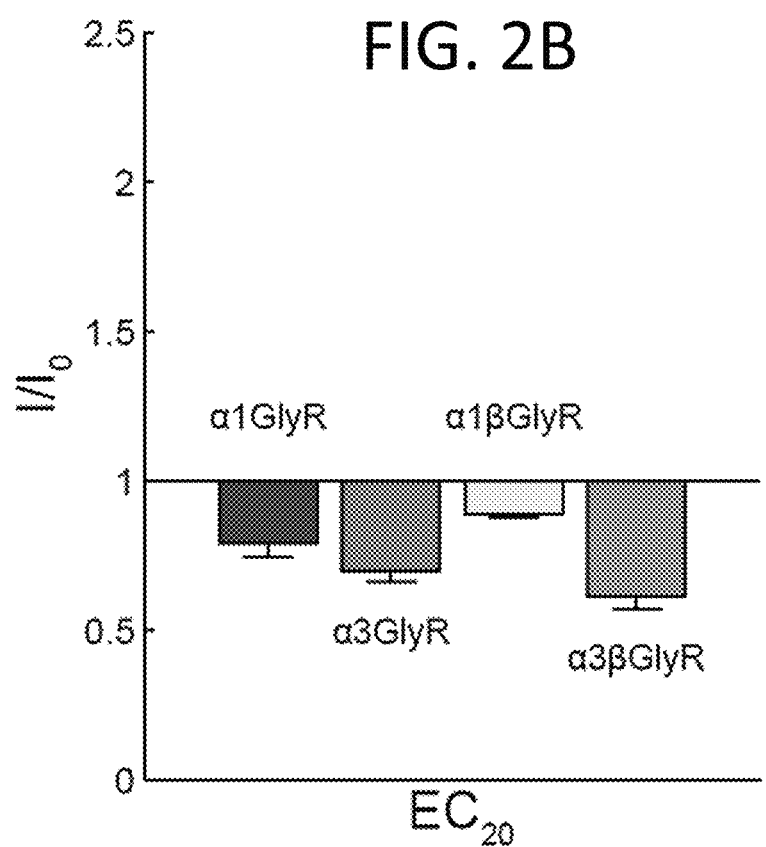
Figure 3A:
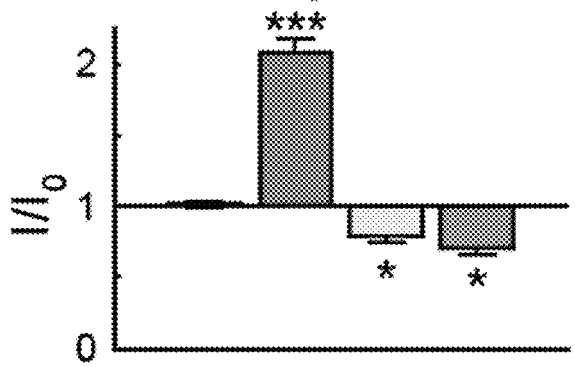
FIGS. 3A-3H are bar graphs showing the modulation of several disclosed compounds on human glycine receptor subtypes (α1GlyR—1$^{st}$ and 3$^{rd}$ bars, and α3GlyR—2$^{nd}$ and 4$^{th}$ bars) expressed in *Xenopus laevis* oocytes activated by 2% (1$^{st}$ and 2$^{nd}$ bars) or 20% (3$^{rd}$ and 4$^{th}$ bars) maximal effective concentration of glycine. The assessed compounds were compound 1 (3A), 2 (3B), 3 (3C), 4 (3D), 5 (3E), 6 (3F), 7 (3G), and 8 (3H).
Figure 3B:
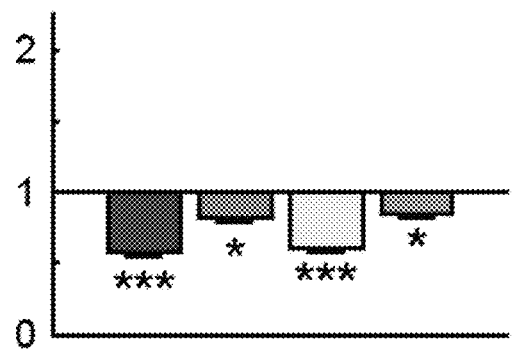
Figure 3C:
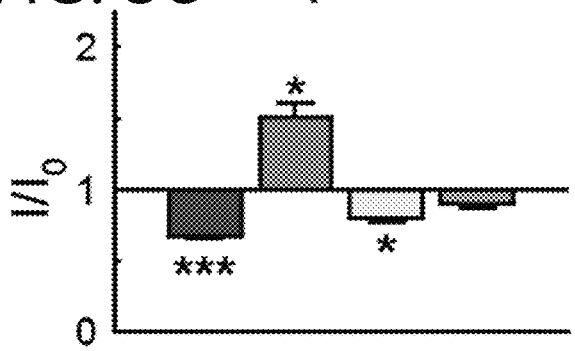
Figure 3D:
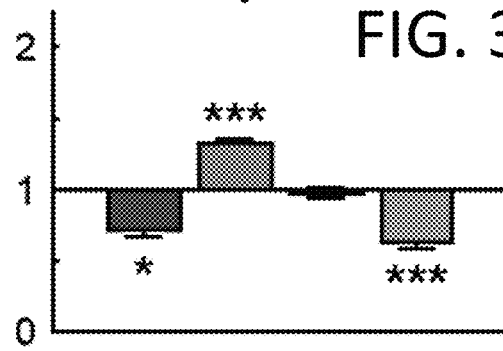
Figure 3E:
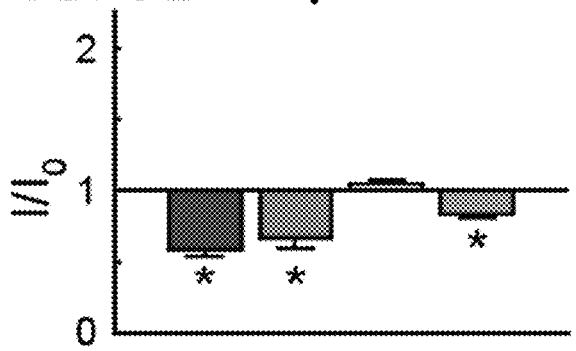
Figure 3F:
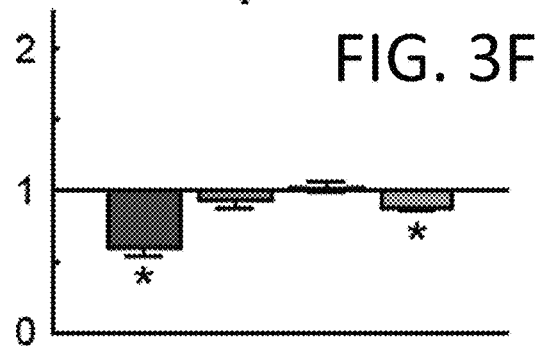
Figure 3G:
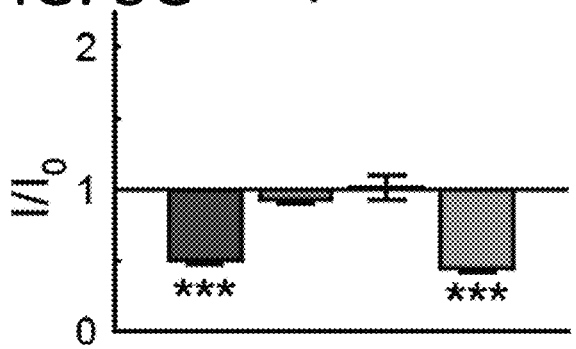
Figure 3H:
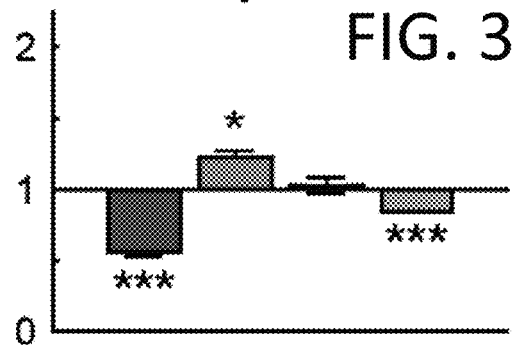

FIGS. 2A and 2B are bar graphs showing the effect of compound 1 on modulation of human glycine receptor subtypes (α1GlyR, α3GlyR, α1βGlyR, and α3βGlyR) expressed in *Xenopus laevis* oocytes activated by 2% (FIG. 2A) and 20% (FIG. 2B) maximal effective concentration of glycine. $I/I_o$ was calculated as the ratio of the current measured in the presence (I) and absence ($I_o$) of 10 μM compound 1. Error bars designate the standard error of the mean (n≥4).

The compounds disclosed in Table 1 were assessed for in vitro modulation of human GlyRs. FIGS. 3A-3H are bar graphs showing the effects of the compounds on modulation of human glycine receptor subtypes (α1GlyR—$1^{st}$ and $3^{rd}$ bars, and α3GlyR—$2^{nd}$ and $4^{th}$ bars) expressed in *Xenopus laevis* oocytes activated by 2% ($1^{st}$ and $2^{nd}$ bars) or 20% ($3^{rd}$ and $4^{th}$ bars) maximal effective concentration of glycine. The assessed compounds were compounds 1 (3A), 2 (3B), 3 (3C), 4 (3D), 5 (3E), 6 (3F), 7 (3G), and 8 (3H). $I/I_o$ was calculated as the ratio of the current measured in the presence (I) and absence ($I_o$) of 10 μM of the indicated compound. Stars indicate significant modulation ($I/I_o \neq 1$) at p<0.033 (*), p<0.002 (), or p<0.001 (*). Error bars designate the standard error of the mean (n≥4).

Example 2

Pain Modulation

Figure 4:
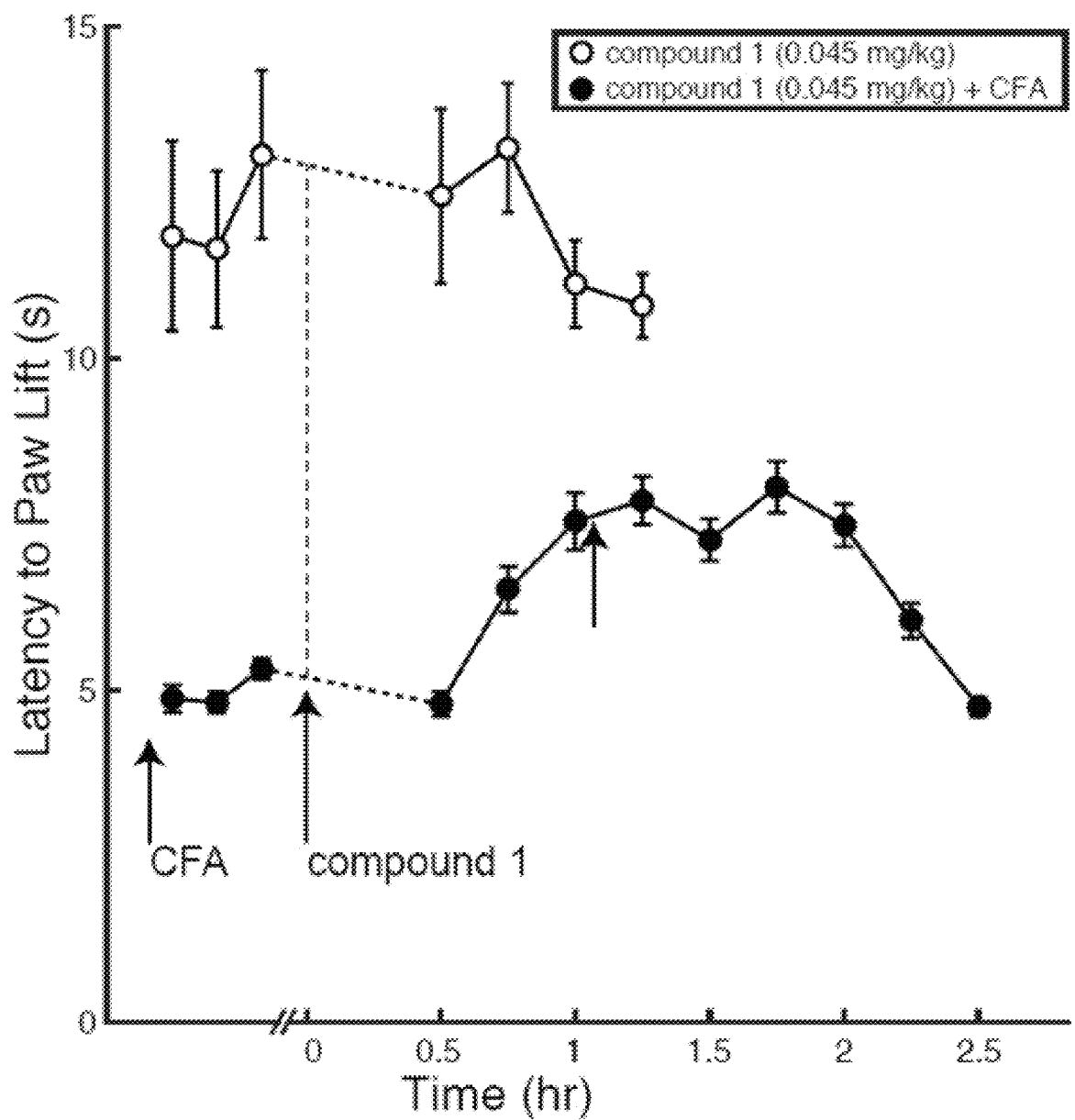
FIG. 4 is a graph showing an increase in response time (decrease in pain sensation) in $C_{57}$Bl/6J mice to the Hargreaves test under compete Freund's adjuvant (CFA)-induced hyperalgesic conditions after administration of compound 1.

In vivo mouse behavior tests validated the analgesic action of the representative compounds in response to inflammation. Responses of $C_{57}Bl/6J$ mice to the Hargreaves test (Pain, 32:77-88, 1988) were assessed pre- and post-application of compound 1 alone (white circles, application time=0 hours). As shown in FIG. 4, compound 1 administered under normal nociceptive conditions had no significant effect on response time for paw withdrawal. However, under maximum CFA-induced hyperalgesic conditions (24 hours post-application of CFA), treatment with compound 1 led to an increase in response time, i.e., a decrease in the sensation of inflammatory pain (black circles, compound 1 application time=0 hours). Error bars designate the standard error of the mean (n≥4).

Figure 5:
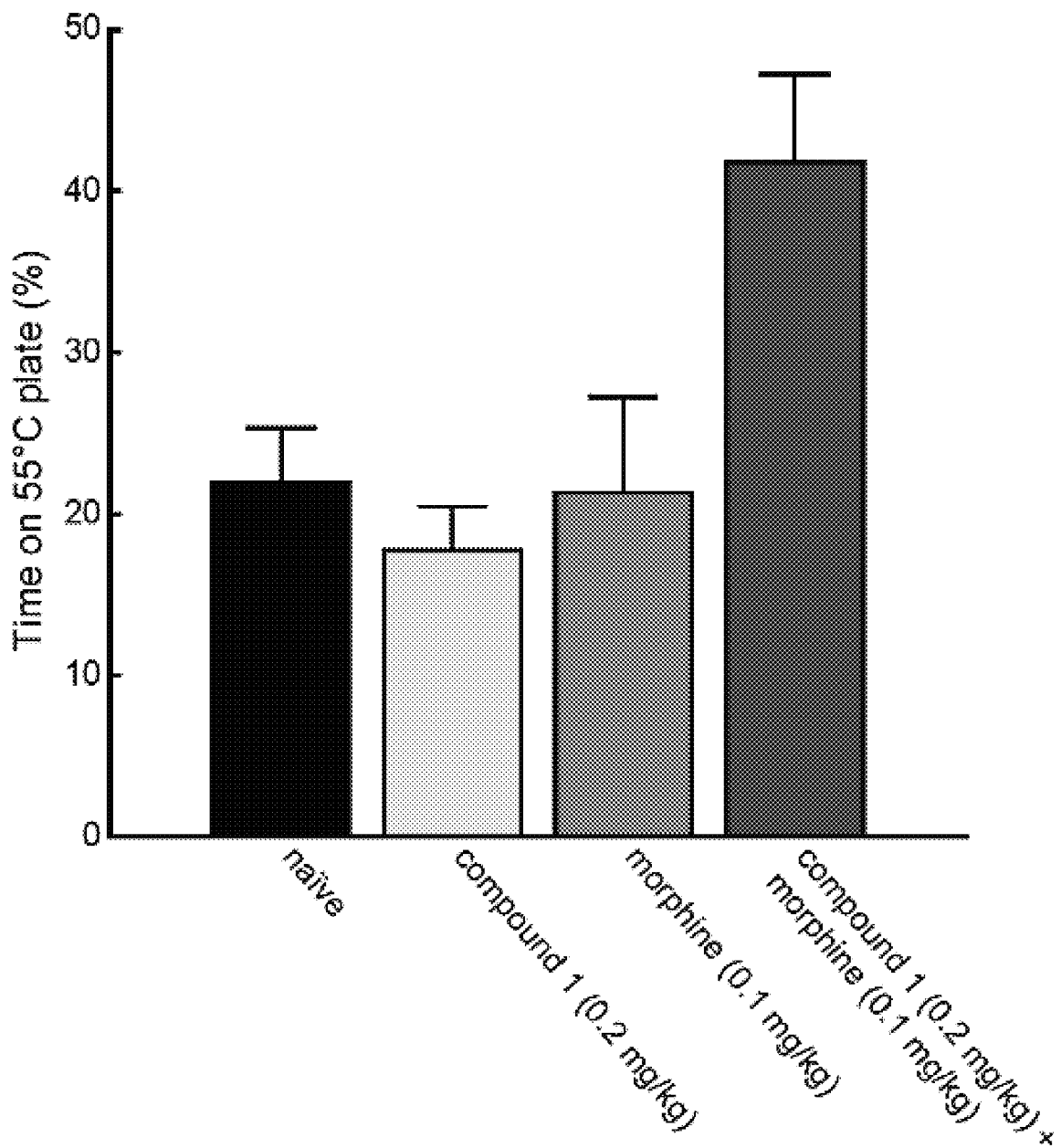
FIG. 5 is a bar graph showing synergistically increased pain tolerance in mice during a two-plate thermal preference test when combining compound 1 with morphine.

In vivo mouse behavior tests revealed synergistic effects of the representative compound in combination with opioids. Different concentration combinations are possible, ranging from subclinical concentrations of opioids (e.g., 0.1-1 mg/kg morphine) with 0.01-1 mg/kg compound 1. Examples of nociceptive response are depicted in FIG. 5.

Responses to the two-plate thermal preference test were assessed under naïve conditions and 1 hour after administration of 0.2 mg/kg compound 1, 0.1 mg/kg morphine, or 0.2 mg/kg compound 1+0.1 mg/kg morphine. Unrestrained mice were exposed to plates set to normal and hot temperatures (30° C. and 55° C., respectively). Temperature preference was measured by percentage time spent on the hot plate (55° C.) over the course of 4 minutes, where 50% indicates no preference between the two temperatures. The co-application of low doses of compound 1 and morphine led to a significant increase in time spent on the "uncomfortable" hot plate compared to naïve mice, indicating a decreased nociceptive response to thermal pain (p<0.005). Treatment with either compound 1 or morphine alone showed no significant analgesic response compared to naïve mice in normal nociception. Error bars designate the standard error of the mean (n≥5).

Figure 6:
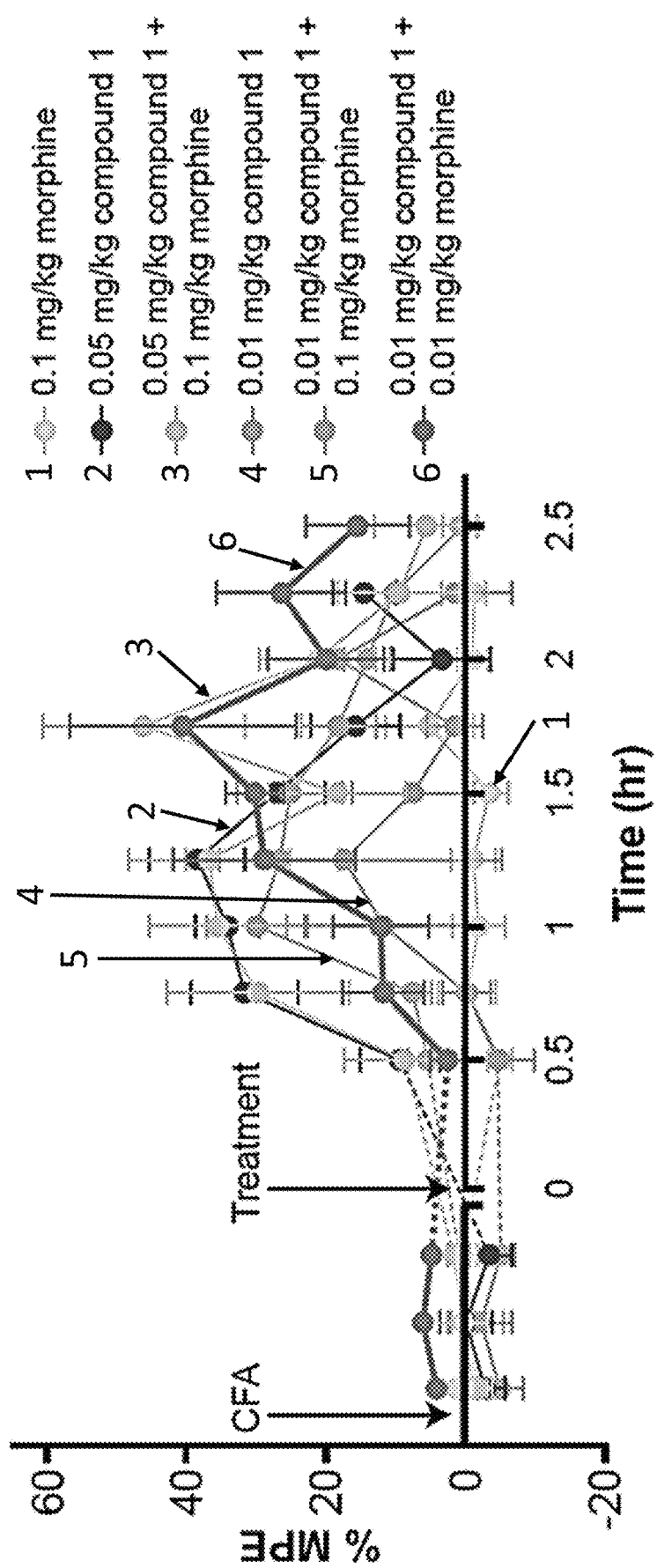
FIG. 6 is a graph showing increased pain tolerance in mice under CFA-induced hyperalgesic conditions after administration of compound 1 in combination with morphine.

FIG. 6 shows the effects on mice of varying dosages of compound 1 and morphine (application time=0 hours) under maximum CFA-induced hyperalgesic conditions (24 hours post-application of CFA), demonstrating that larger analgesic effects were observed when combining low doses of compound 1 and morphine compared to either compound alone. Under CFA-induced hyperalgesic conditions, the maximum possible effect, % MPE=(response−baseline)/(cut-off time−baseline), was measured for the application of compound 1 alone (0.05 mg/kg, blue, n=12; 0.01 mg/kg, orange, n=4), morphine alone (0.1 mg/kg, green, n=8), and compound 1 with morphine at three different dosage combinations: 0.05 mg/kg compound 1 with 0.1 mg/kg morphine (light blue, n=6), 0.01 mg/kg compound 1 with 0.1 mg/kg morphine (pink, n=10), and 0.01 mg/kg compound 1 with 0.01 mg/kg morphine (red, n=4). Larger, synergistic analgesic effects were observed for 0.01 mg/kg compound 1 with 0.01 mg/kg morphine compared to either 0.01-0.05 mg/kg compound 1 or 0.1 mg/kg morphine alone, particularly at times greater than ~1.5 hours after administration. Error bars designate the standard error of the mean.

Figure 7A:
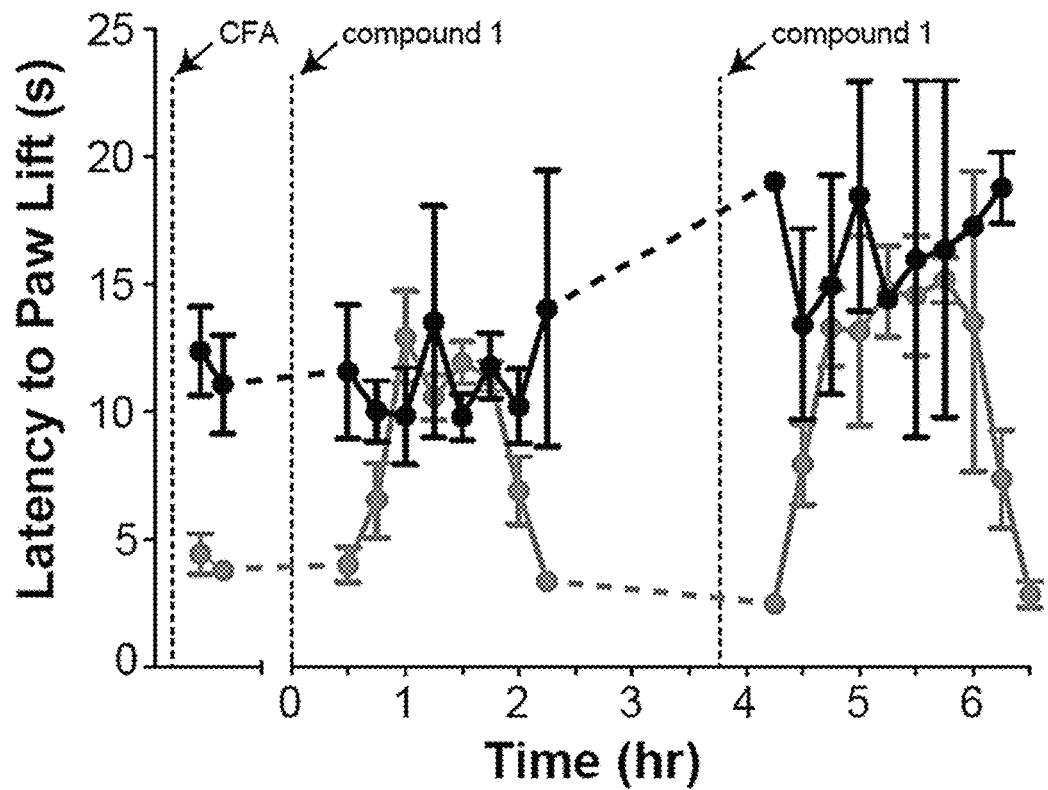
FIGS. 7A and 7B are graphs showing that repeated doses of compound 1 herein do not generate tolerance in mice under CFA-induced hyperalgesic conditions. A repeated dose was administered 1.5 hours (7A) or 24 hours (7B) after the effects of a first dose wore off.
Figure 7B:
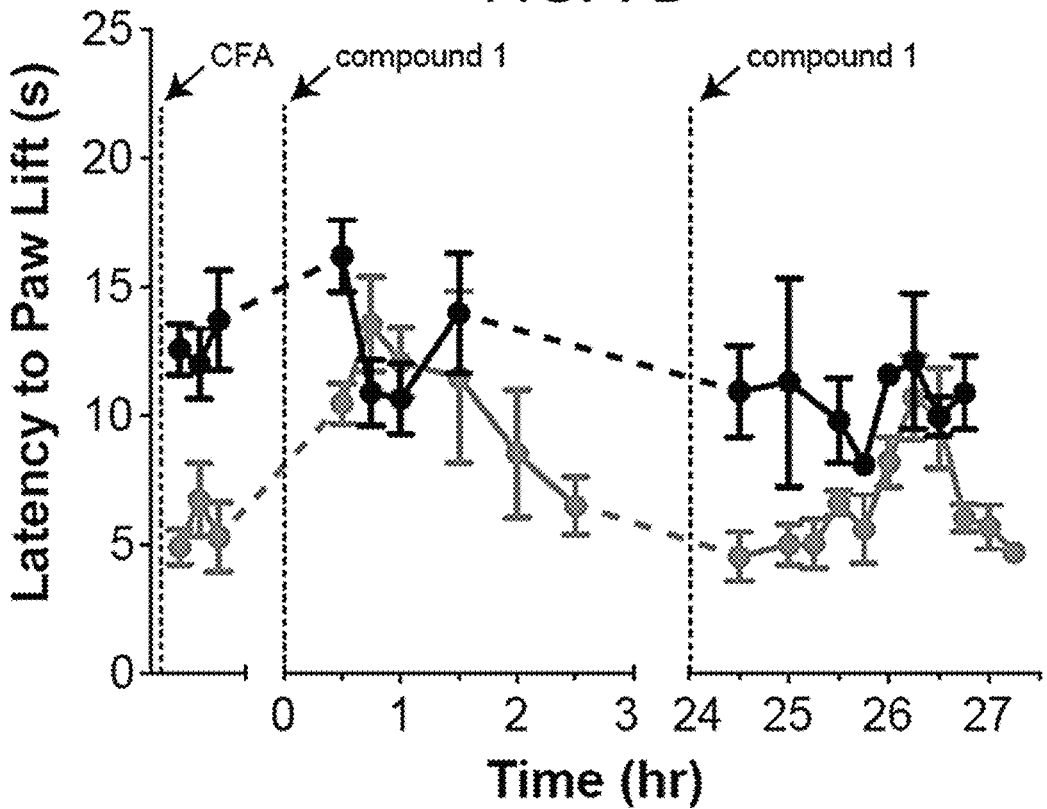

Repeated doses of compound 1 do not generate tolerance as shown in FIGS. 7A and 7B. 0.05 mg/kg compound 1 was tested for tolerance in CFA-treated mice (red). Under CFA-induced hyperalgesic conditions (24 hours post-application of CFA), 0.05 mg/kg compound 1 was administered to CD1 mice and responses to the Hargreaves test were measured immediately after the initial injection (application time=0) and again after a repeated dose given 1.5 hours (FIG. 7A) or 24 hours (FIG. 7B) after the effects of the first dose wore off. The black circles represent the responses of naïve mice (i.e., no administration of compound 1 or CFA), and the red circles represent the responses of mice receiving compound 1 under CFA-induced hyperalgesic conditions. No tolerance was observed as the time to paw withdrawal did not significantly change between the first and second dosing. Error bars designate the standard error of the mean (n=4).

Responses of CD1 mice to the Hargreaves test were assessed after application of 0.1 mg/kg of the indicated compounds (black) or vehicle (white) under CFA-induced hyperalgesic conditions as shown in FIGS. 8A-8H. The assessed compounds were compounds 1 (8A), 2 (8B), 3 (8C), 4 (8D), 5 (8E), 6 (8F), 7 (8G), and 8 (8H). Treatment with each representative compound at time=0 led to an increase in the response time for paw withdrawal, i.e. a decrease in the sensation of inflammatory pain. Stars indicate significant increases compared to vehicle after the time point indicated for each compound at $p<0.033$ (*), $p<0.002$ (), or $p<0.001$ (*) by repeated measures one-way ANOVA and Dunnett's multiple comparisons test. Error bars designate the standard error of the mean (n≥4).

Compound 3 was demonstrated to provide prolonged analgesic effects, even after 48 hours. Under CFA-induced hyperalgesic conditions, responses of CD1 mice to the two-plate thermal preference test were assessed under naïve conditions (white), 0.1 mg/kg of compound 3 (black), or 0.1 mg/kg compound 4 (grey) 1 and 48 hours after intraperitoneal injection, as shown in FIG. 9. Unrestrained mice were exposed to plates set to normal and hot temperatures (30° C. and 55° C., respectively) for 10 minutes. Thermal tolerance was measured by the percentage of inactive time on the hot plate (55° C.). Error bars designate the standard error of the mean (n=4). Application of compound 3 significantly increased the inactive time spent on the hot plate, even 48 hours after injection, indicating a prolonged analgesic effect. Application of compound 4 also showed an increase in the inactive time spent on the hot plate 1 hour after injection, but no effect 48 hours later. Stars indicate significant increases compared to naïve at $p<0.05$ (*) or $p<0.01$ (**) by Least Significant Difference post-hoc test.

Figure 10:
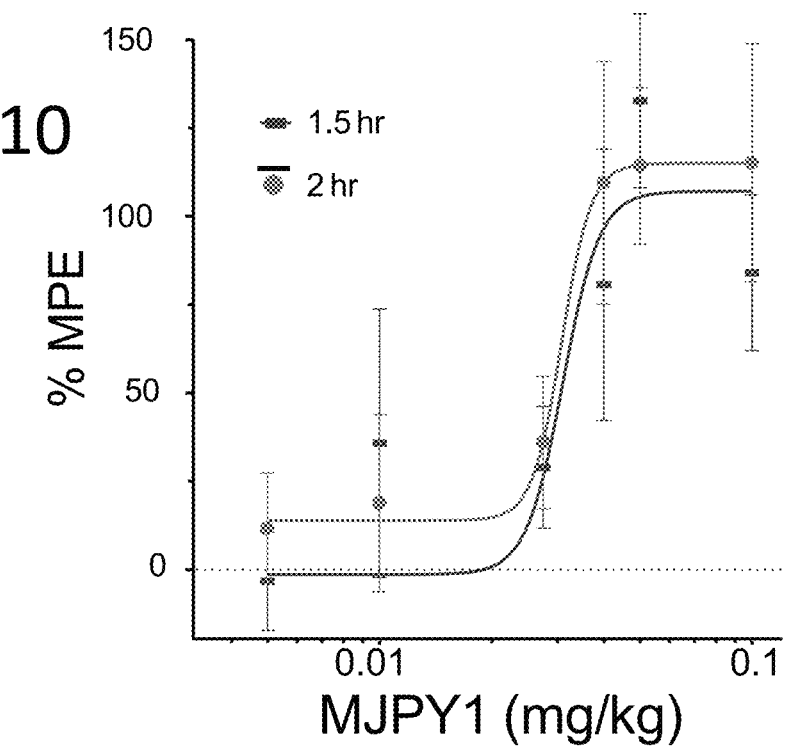
FIG. 10 is an in vivo dose response curve for compound 1 (identified as MJPY1 in FIG. 10) showing that the EC50 for inflammatory pain is ~0.03 mg/kg in CD1 mice.

FIG. 10 shows the in vivo efficacy and potency of compound 1 (identified as MJPY1). Dose response curves from the Hargreaves test in mice with a CFA-inflamed left hind paw at 1.5 and 2 hr after intraperitoneal injection of compound 1. Percent Maximum Possible Effect (% MPE) was calculated from paw withdrawal latencies. Data from 33 CFA-inflamed and 14 naïve mice (mean±SEM) are fitted to the Hill equation, yielding EC50~0.030 mg/kg at both time points.

Figure 11:
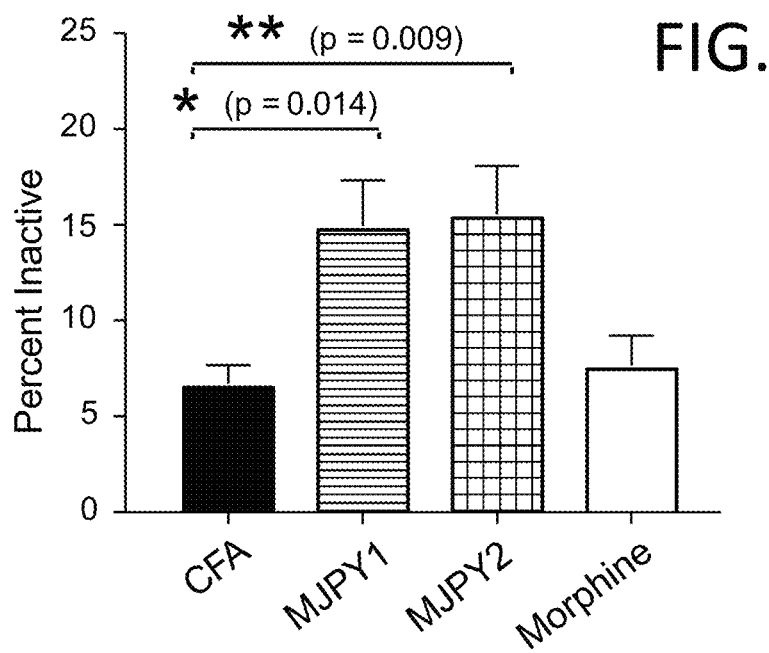
FIG. 11 is a bar graph demonstrating that the analgesic action of compound 1 (identified as MJPY1) and compound 3 (identified as MJPY2) was better than morphine under the same dose in the non-invasive thermal preference test in mice.

FIG. 11 shows the analgesic effects of 0.1 mg/kg of compound 1 (identified as MJPY1 in FIG. 11) and compound 3 (identified as MJPY2 in FIG. 11), and morphine on inflammatory pain in male CD1 mice (n=4/group), measured by the 55° C. vs. 30° C. thermal preference test 24 hr after intraplantar CFA injection and 1 hr after i.p. drug treatment. The percent inactivity on the 55° C. plate (mean±SEM) is a measure of heat tolerance. Significance was assessed by one-way ANOVA with LSD post-hoc test.

Figure 12:
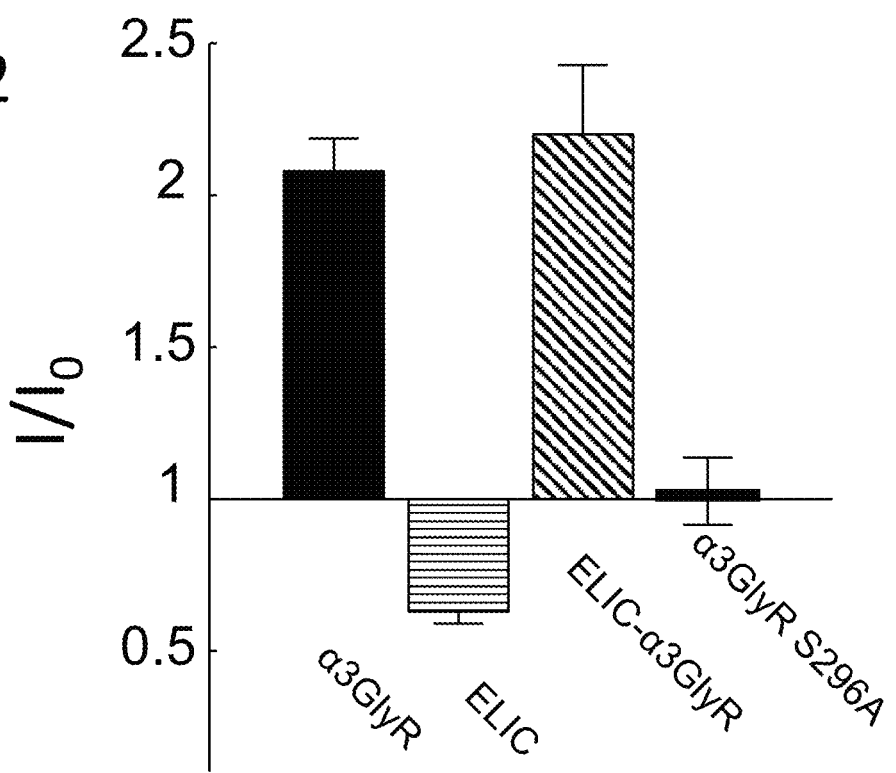
FIG. 12 is a bar graph showing that compound 1 potentiates α3GlyR through binding to the THC-binding site near S296 in the transmembrane domain (TMD).

FIG. 12 shows the in vitro effects of compound 1 (MJPY1) measured by electrophysiology on *Xenopus laevis* oocytes. MJPY1 potentiates α3GlyR through binding to the THC-binding site near S296 in the transmembrane domain (TMD). Like α3GlyR, but unlike ELIC, the chimera ELIC-α3GlyR containing the α3GlyR TMD is potentiated by MJPY1. The S296A mutation in α3GlyR abolishes compound 1 (MJPY1)'s potentiation. Data were recorded at $EC_2$ agonist for the indicated channels and are reported as the ratio of currents in the presence (I) and absence ($I_o$) of 10 μM compound 1 (MJPY1). Error bars represent SEM (n≥4 oocytes).

Figure 13:
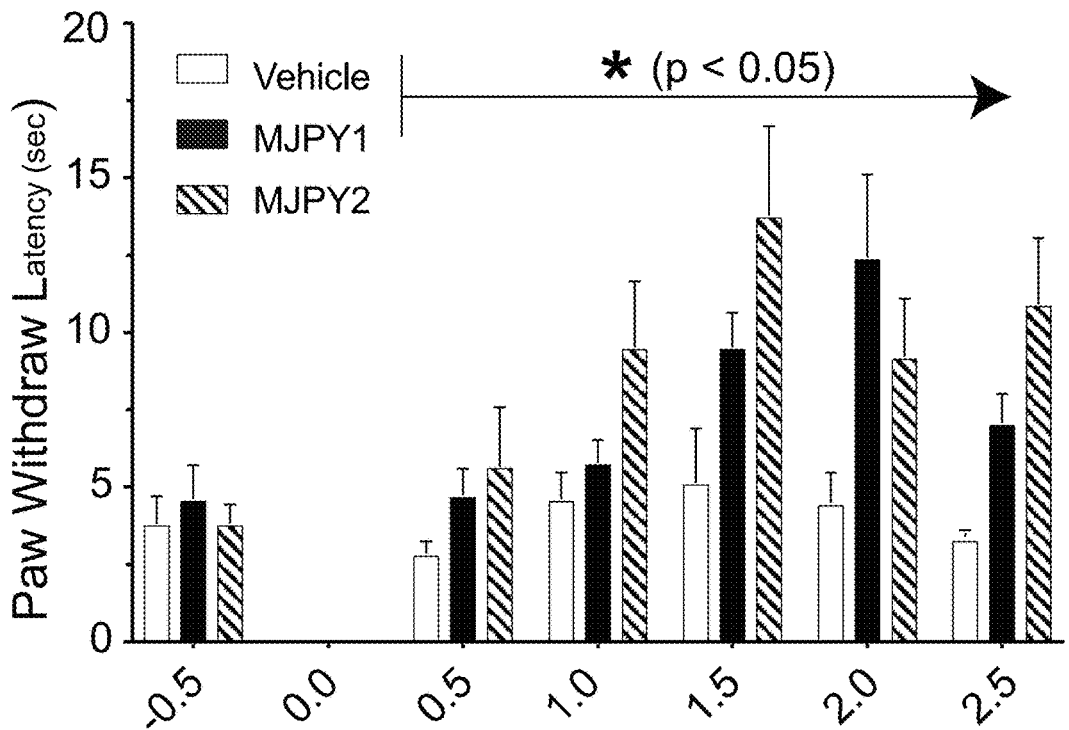
FIG. 13 is a bar graph demonstrating that the analgesic efficacies of compound 1 (identified as MJPY1) and compound 3 (identified as MJPY2) did not decrease after repeated drug exposure.

Tolerance to compound 1 (MJPY1) and compound 3 (MJPY2) was measured by repeated dosing in the Hargreaves Test. FIG. 13 shows the negligible tolerance to either compound 1 (MJPY1) or compound 3 (MJPY2). Mice (n=6/group) received repeated i.p. injections of vehicle or 0.1 mg/kg compound 1 (MJPY1) or compound 3 (MJPY2) once a day for 5 days. CFA inflammation was induced on day 4, and PWL was measured 0.5 hr before and every 10 min after treatment on day 5. Data were binned to 30-min blocks (mean±SEM). There was no measurable tolerance from repeated drug exposure, as shown by repeated measures ANOVA with LSD post-hoc test.

Figure 14:
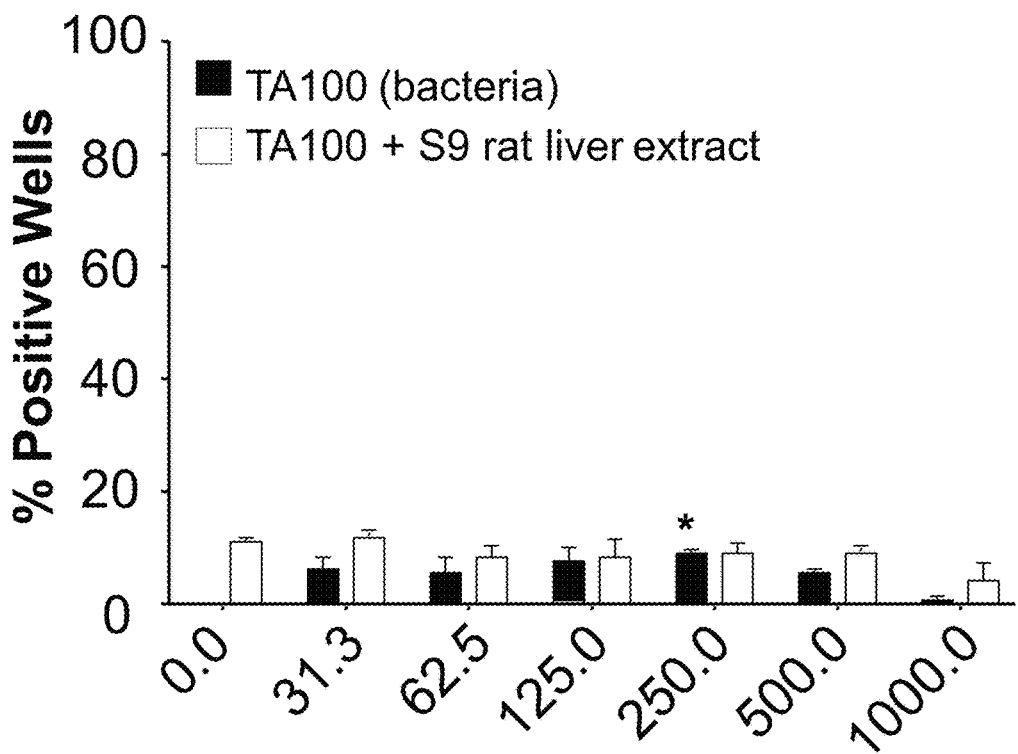
FIG. 14 is a bar graph showing no mutagenic activity from compound 1 in the in vitro Ames toxicity test.
Figure 15A:
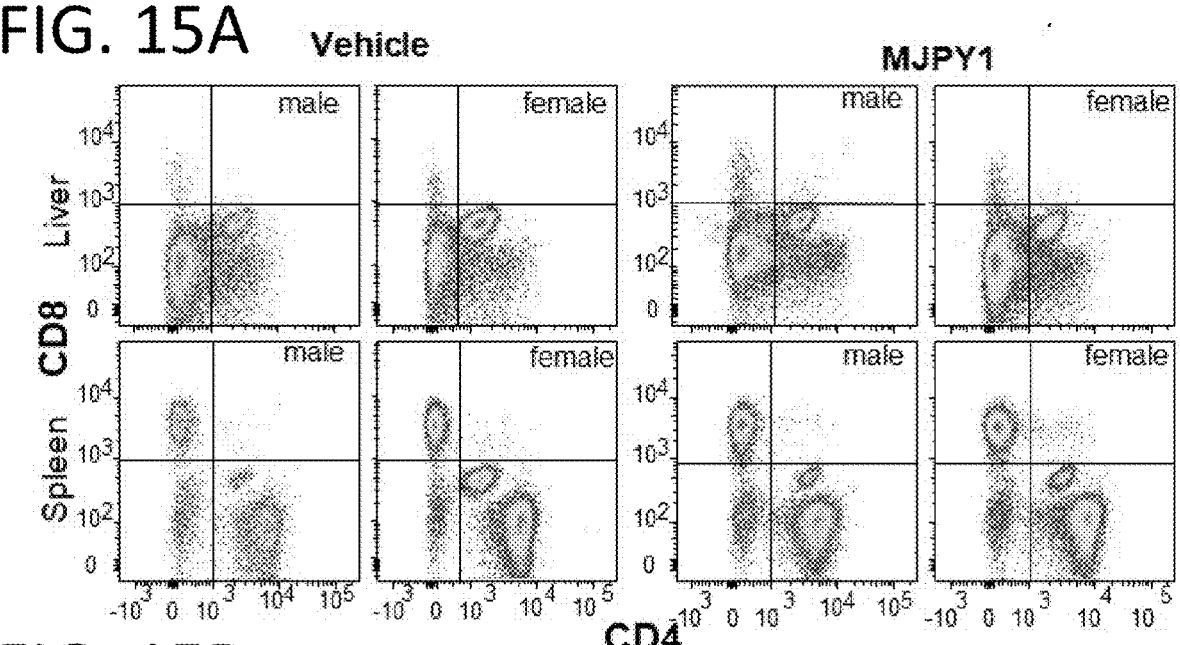
FIGS. 15A-B are scatter plots showing the in vivo immune responses from flow cytometry from mice exposed to compound 1.
Figure 15B:
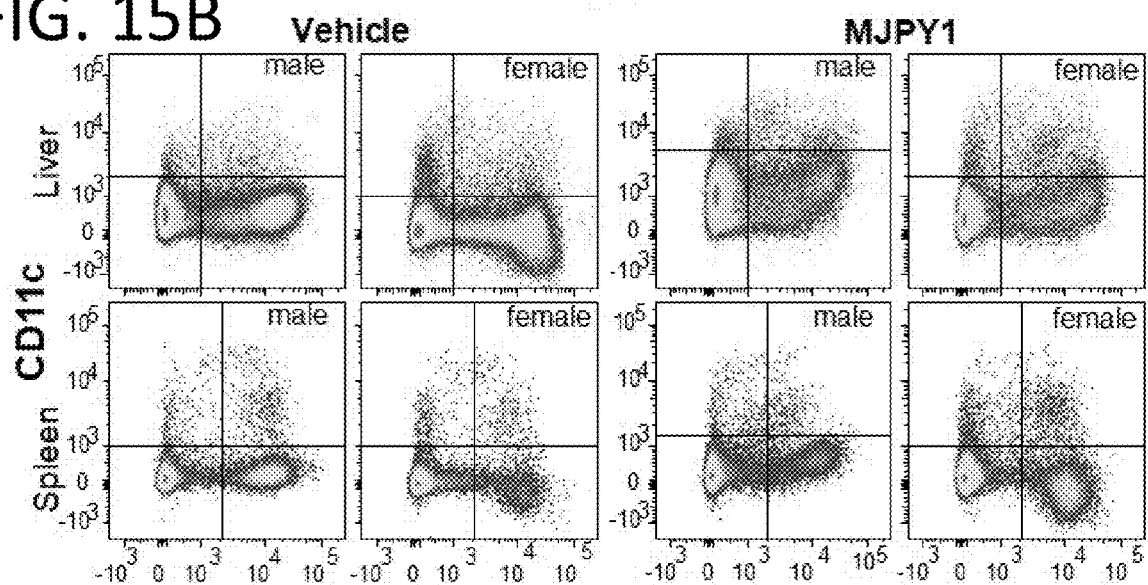

Toxicity was evaluated using in vitro Ames test and in vivo immune responses flow cytometry. Ames tests revealed compound 1 (MJPY1) and its potential metabolites have little mutagenic activity, as shown in FIG. 14. Compound 1 (MJPY1) at each concentration was tested in three 48-well plates using the TA100 strain *Salmonella typhimurium* and S9 rat liver extract for base-pair substitution mutations. Error bars represent SEM. Significance ($p<0.05$) was evaluated compared to the control (0 μM) using one-way ANOVA with the Bonferroni post-hoc test. FIGS. 15A and 15B show flow cytometry evaluation of common inflammatory markers in the liver and spleen of mice in response to compound 1 (MJPY1) treatment. Mice received either 2 mg/kg of MJPY1 (right) or vehicle (left) ~16 hours prior to sacrifice and tissue collection. Analysis of regulatory (CD4+) and cytotoxic (CD8+) T cells is shown in FIG. 15A. Analysis of dendritic cells, monocytes, and macrophages via CD11b+ and CD11c+ markers is shown in FIG. 15B. Significant differences between the treatment and control were observed only for decreased CD11b+ in the liver of mice treated with MJPY1 ($p<0.001$). Overall, these results suggest a minimal immune response to MJPY1 treatment. Results were analyzed by one-way ANOVA with Bonferroni post-hoc test.

Figure 16:
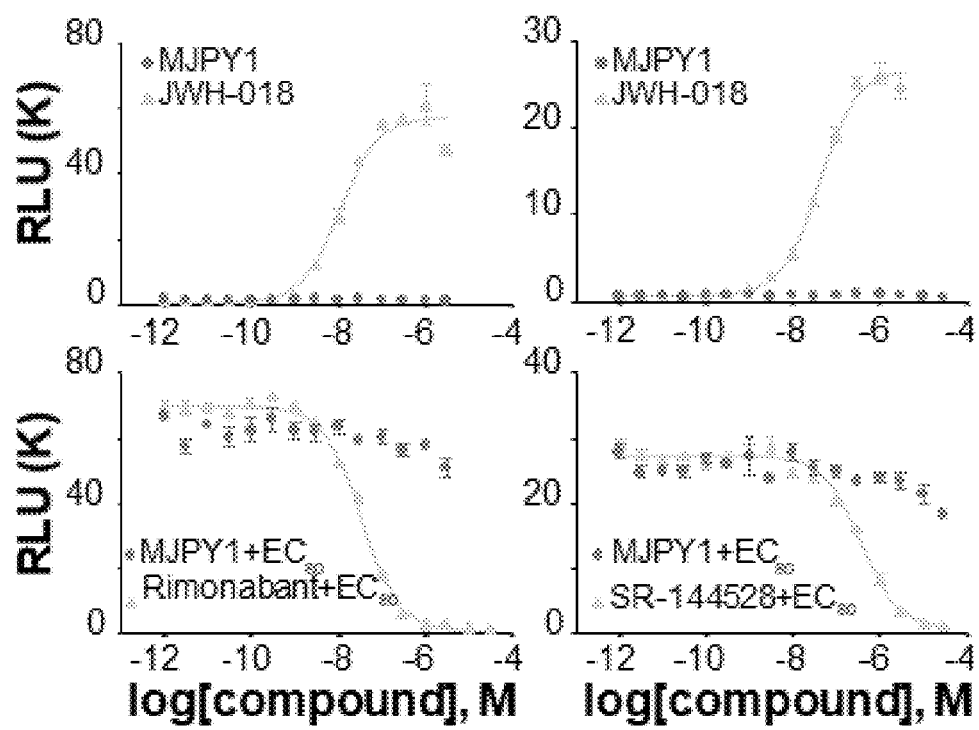
FIG. 16 is a graph showing that compound 1 has no activity on cannabinoid receptors.

The specificity of compound 1 (MJPY1) to act only on glycine receptors was determined. No cross reactivity with other commonly known receptors was detected (FIG. 16 and Table 2). Specifically, compound 1 (MJPY1) shows no agonist (top) or antagonist (bottom) activity on both CB1 (left) and CB2 (right) receptors in PRESTO-TANGO functional assays against positive controls (FIG. 16). Activity is reported in relative luminescence units (RLU) as mean and SEM (n=3).

TABLE 2

Off-target profiling of MJPY1. Radioligand binding assays reported the mean % inhibition by 10 M MJPY1 on the listed targets (n = 4). Inhibition >50% is considered significant. Negative inhibition represents non-specific stimulation of binding. MJPY1 shows no significant cross-reactivity for any tested targets.

| Target | 4 2-nAChR | 5-$HT_3$R | DOR | KOR | MOR | NOR | NMDAR | hERG |
|---|---|---|---|---|---|---|---|---|
| % Inhibition | −1.8 | −5.7 | 7.1 | 5.0 | 20.6 | −16.8 | −2.4 | −19.5 |

Example 3

Pain Reduction

A subject having pain or in need of prophylaxis for pain is identified and selected. The subject may be identified and selected based on a clinical presentation or based on an upcoming treatment expected to produce pain (e.g., surgery). The subject is administered a compound according to formula I or a stereoisomer, tautomer, or pharmaceutically acceptable salt thereof as disclosed herein at amounts determined by a clinician to be therapeutically effective.

A second therapeutic agent may be co-administered with the compound. The second therapeutic agent may be administered either separately or together in a pharmaceutical composition with the compound. The second therapeutic agent may be administered by the same route or a different route. If administered concurrently, the compound and the second therapeutic agent may be combined in a single pharmaceutical composition or may be administered concurrently as two pharmaceutical compositions. The second therapeutic agent may be, for example, an opioid, analgesic, nonsteroidal anti-inflammatory drug (NSAID), COX-2 inhibitor, cannabinoid, antidepressant, local anesthetic, or anti-inflammatory steroid, or any combination thereof.

Example 4

Treatment of Opioid Addiction and/or Reduction of Side Effects Attributable to Opioid Use A subject addicted to opioids, suffering side effects attributable to opioid use, or at risk of opioid addiction or opioid-induced side effects is identified and selected. The subject may be selected based on a clinical presentation, based on an assessment (e.g., a questionnaire regarding opioid use and/or side effects), or based on a condition or upcoming treatment expected to result in opioid use. The subject is administered a compound according to formula I or a stereoisomer, tautomer, or pharmaceutically acceptable salt thereof as disclosed herein at amounts determined by a clinician to be therapeutically effective.

An opioid may be co-administered with the compound. The opioid may be administered either separately or together in a pharmaceutical composition with the compound. The opioid may be administered by the same route or a different route. If administered concurrently, the compound and the opioid may be combined in a single pharmaceutical composition or may be administered concurrently as two pharmaceutical compositions. The opioid may be administered at a subclinical/subtherapeutic dose. In some instances, the opioid dosage may begin at a therapeutically effective dose or a given subtherapeutic dose and then gradually decreased over a period of time until the subject is no longer receiving the opioid, thereby weaning the subject off the opioid.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for treating opioid addiction and/or reducing side effects attributable to opioid use in a subject, comprising: administering to the subject an effective amount of a compound having a structure according to formula I, or a stereoisomer, tautomer, or pharmaceutically acceptable salt thereof:

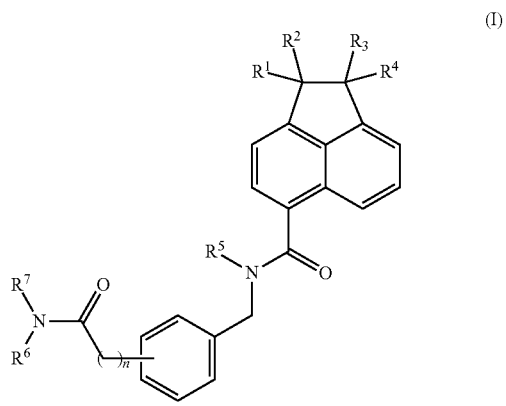

(I)

where $R^1$, $R^2$, $R^3$, and $R^4$ independently are hydrogen, halo, or hydroxy;

$R^5$ is hydrogen, halo, $C_1$-$C_{10}$ alkyl, or hydroxy;

$R^6$ and $R^7$ independently are hydrogen, halo, hydroxy, $C_1$-$C_{10}$ alkyl, or $C_1$-$C_{10}$ alkyl carboxamide, or $R^6$ and $R^7$ together with the nitrogen to which they are bound form a heterocycloaliphatic or heteroaryl group; and n is 0, 1, 2, or 3.

2. The method of claim 1, wherein administering the effective amount of the compound or pharmaceutically acceptable salt thereof comprises administering an amount of a pharmaceutical composition comprising the effective amount of the compound to the subject.

3. The method of claim 1, further comprising co-administering the compound and a second therapeutic agent to the subject, wherein the second therapeutic agent is an opioid, nonsteroidal anti-inflammatory drug, COX-2 inhibitor, cannabinoid, antidepressant, local anesthetic, or anti-inflammatory steroid.

4. The method of claim 3, wherein co-administering comprises administering simultaneously or sequentially in any order.

5. The method of claim 3, wherein the compound and the second therapeutic agent are simultaneously administered to the subject in a single pharmaceutical composition.

6. The method of claim 3, wherein the compound and the second therapeutic agent are administered in separate pharmaceutical compositions by the same or different routes of administration.

7. The method of claim 3, wherein:
   (i) the effective amount of the compound is within a range of from 0.001-100 mg/kg body weight;
   (ii) the second therapeutic agent is an opioid, and the opioid is administered in a subclinical amount; or
   (iii) both (i) and (ii).

8. The method of claim 1, wherein the compound has a structure according to formula II or formula III:

(II)

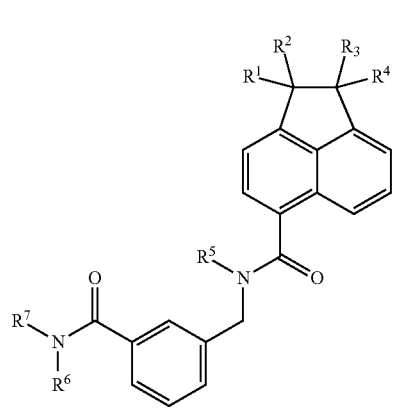

(III)

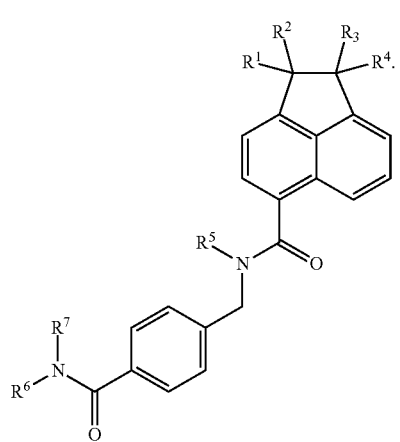

9. The method of claim 1, wherein $R^1$-$R^4$ are hydrogen.

10. The method of claim 1, wherein $R^5$ is hydrogen, halo, $C_1$-$C_5$ alkyl, or hydroxy.

11. The method of claim 1, wherein $R^6$ and $R^7$ independently are hydrogen, halo, methyl, ethyl, propyl, isopropyl, hydroxy, or —$CH_2C(O)NH_2$, or $R^6$ and $R^7$ together with the nitrogen to which they are bound form a substituted or unsubstituted piperidinyl or piperazinyl group.

12. The method of claim 1, wherein the compound is

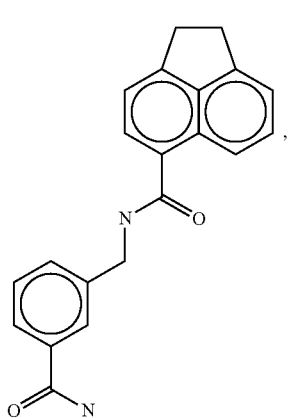

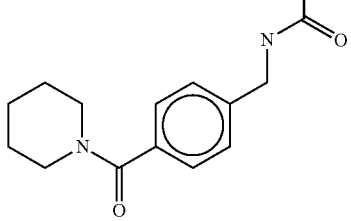

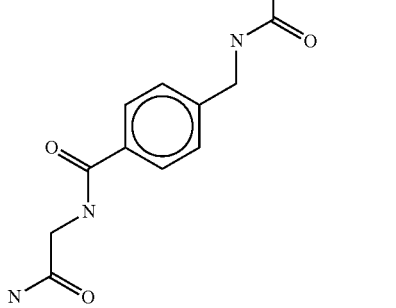

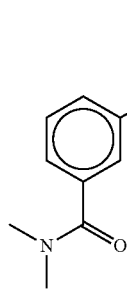

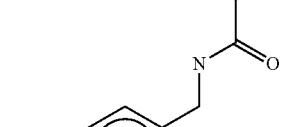

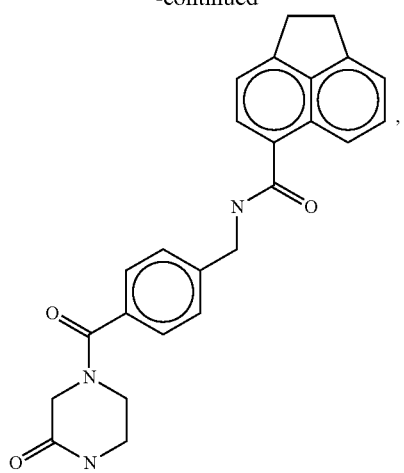

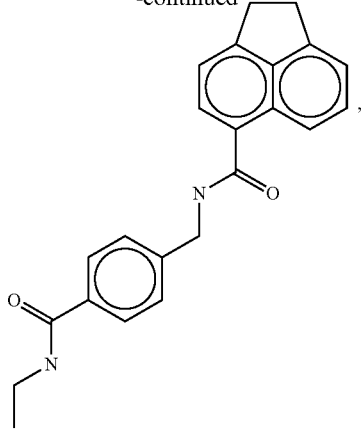

or any combination thereof.

13. The method of claim 1, wherein the compound is or any combination thereof.

14. The method of claim 8, further comprising co-administering the compound and a second therapeutic agent to the subject, wherein the second therapeutic agent is an opioid, nonsteroidal anti-inflammatory drug, COX-2 inhibitor, cannabinoid, antidepressant, local anesthetic, or anti-inflammatory steroid.

15. The method of claim 1, wherein $R^6$ and $R^7$ are each hydrogen.

16. The method of claim 1, wherein $R^5$ is hydrogen.

17. The method of claim 9, wherein $R^5$ is hydrogen.

* * * * *